(12) United States Patent
Larsen et al.

(10) Patent No.: US 9,662,153 B2
(45) Date of Patent: May 30, 2017

(54) GUIDE ASSEMBLY FOR INTRAMEDULLARY FIXATION AND METHOD OF USING THE SAME

(71) Applicant: Wright Medical Technology, Inc., Arlington, TN (US)

(72) Inventors: Scott Larsen, Devon, PA (US); Virak Tan, New Providence, NJ (US); Mark J. Warburton, High Point, NC (US)

(73) Assignee: Wright Medical Technology, Inc., Memphis, TN (US)

( * ) Notice: Subject to any disclaimer, the term of this patent is extended or adjusted under 35 U.S.C. 154(b) by 384 days.

(21) Appl. No.: 14/271,067

(22) Filed: May 6, 2014

(65) Prior Publication Data
US 2014/0243839 A1 Aug. 28, 2014

Related U.S. Application Data

(62) Division of application No. 11/957,742, filed on Dec. 17, 2007, now Pat. No. 8,771,283.

(51) Int. Cl.
*A61B 17/17* (2006.01)
*A61B 17/72* (2006.01)
(Continued)

(52) U.S. Cl.
CPC .......... *A61B 17/72* (2013.01); *A61B 17/1725* (2013.01); *A61B 17/1782* (2016.11);
(Continued)

(58) Field of Classification Search
CPC ............ A61B 17/1725; A61B 17/1782; A61B 2017/90; A61B 17/921
See application file for complete search history.

(56) References Cited

U.S. PATENT DOCUMENTS 2,500,370 A 3/1950 McKibbin
2,682,265 A 6/1954 Collison
(Continued)

FOREIGN PATENT DOCUMENTS

DE 7 115 713 6/1975
DE 8 533 134.1 11/1985
(Continued)

OTHER PUBLICATIONS

"The Next Generation in Nail Fixation: Symposium: Current Concepts in Femoral Nailing," vol. 26(2) (1993), 35 pages.
(Continued)

*Primary Examiner* — David Bates
(74) *Attorney, Agent, or Firm* — Knobbe Martens Olson & Bear, LLP

(57) ABSTRACT

A guide assembly for facilitating placement of a fixation member within a medullary canal of a radius is provided. According to one embodiment, a guide assembly includes a guide fastener configured to attach to a fixation member and a guide member configured to receive the guide fastener such that the guide member is secured to the fixation member. The guide assembly also includes an interchangeable distal guide member configured to engage and be disengaged from the guide member. The distal guide member defines a plurality of fastener guide openings for guiding respective fasteners through a plurality of fastener openings defined in the fixation member.

19 Claims, 27 Drawing Sheets

(51) Int. Cl.
  *A61B 17/16* (2006.01)
  *A61B 17/92* (2006.01)
  *A61B 17/00* (2006.01)
  *A61B 17/90* (2006.01)
  *A61B 90/00* (2016.01)

(52) U.S. Cl.
  CPC ......... *A61B 17/164* (2013.01); *A61B 17/1686* (2013.01); *A61B 17/1735* (2013.01); *A61B 17/921* (2013.01); *A61B 2017/00915* (2013.01); *A61B 2017/90* (2013.01); *A61B 2090/034* (2016.02); *A61B 2090/062* (2016.02)

(56) References Cited

U.S. PATENT DOCUMENTS

| | | |
|---|---|---|
| 3,334,624 A | 8/1967 | Schneider et al. |
| 3,433,220 A | 3/1969 | Zickel |
| 3,709,218 A | 1/1973 | Halloran |
| 3,781,917 A | 1/1974 | Mathys |
| 3,939,498 A | 2/1976 | Lee et al. |
| 3,973,278 A | 8/1976 | Shersher |
| 3,977,398 A | 8/1976 | Burstein |
| 4,011,863 A | 3/1977 | Zickel |
| 4,055,172 A | 10/1977 | Ender et al. |
| 4,091,806 A | 5/1978 | Aginsky |
| 4,101,985 A | 7/1978 | Baumann et al. |
| 4,103,683 A | 8/1978 | Neufeld |
| 4,135,507 A | 1/1979 | Harris |
| 4,169,470 A | 10/1979 | Ender et al. |
| 4,227,518 A | 10/1980 | Aginsky |
| 4,237,875 A | 12/1980 | Termanini |
| 4,274,754 A | 6/1981 | Cohen |
| 4,338,926 A | 7/1982 | Kummer |
| 4,393,868 A | 7/1983 | Teague |
| 4,423,721 A | 1/1984 | Otte et al. |
| 4,446,857 A | 5/1984 | Otte et al. |
| 4,453,539 A | 6/1984 | Raftopoulos et al. |
| 4,467,793 A | 8/1984 | Ender |
| 4,473,069 A | 9/1984 | Kolmert |
| 4,475,545 A | 10/1984 | Ender |
| 4,483,335 A | 11/1984 | Tornier |
| 4,493,317 A | 1/1985 | Klaue |
| 4,513,744 A | 4/1985 | Klaue |
| 4,522,202 A | 6/1985 | Otte et al. |
| 4,541,424 A | 9/1985 | Grosse et al. |
| 4,590,930 A | 5/1986 | Kurth et al. |
| 4,622,959 A | 11/1986 | Marcus et al. |
| 4,630,601 A | 12/1986 | Harder et al. |
| 4,667,663 A | 5/1987 | Miyata |
| 4,697,585 A | 10/1987 | Williams |
| 4,705,027 A | 11/1987 | Klaue |
| 4,712,541 A | 12/1987 | Harder et al. |
| 4,733,654 A | 3/1988 | Marino |
| 4,775,381 A | 10/1988 | Tari et al. |
| 4,781,181 A | 11/1988 | Tanguy |
| 4,794,919 A | 1/1989 | Nilsson |
| 4,805,607 A | 2/1989 | Engelhardt et al. |
| 4,846,162 A | 7/1989 | Moehring |
| 4,854,312 A | 8/1989 | Raftopoulos et al. |
| 4,858,602 A | 8/1989 | Seidel et al. |
| 4,875,474 A | 10/1989 | Border |
| 4,875,475 A | 10/1989 | Comte et al. |
| 4,877,019 A | 10/1989 | Vives |
| 4,911,153 A | 3/1990 | Border |
| 4,943,291 A | 7/1990 | Tanguy |
| 4,944,764 A | 7/1990 | Stossel |
| 4,946,459 A | 8/1990 | Bradshaw et al. |
| 4,976,258 A | 12/1990 | Richter et al. |
| 4,976,714 A | 12/1990 | Aghion |
| 5,013,314 A | 5/1991 | Firica et al. |
| 5,035,697 A | 7/1991 | Frigg |
| 5,041,115 A | 8/1991 | Frigg et al. |
| 5,057,103 A | 10/1991 | Davis |
| 5,057,110 A | 10/1991 | Kranz et al. |
| 5,066,296 A | 11/1991 | Chapman et al. |
| 5,084,053 A | 1/1992 | Ender |
| 5,100,404 A | 3/1992 | Hayes |
| 5,122,146 A | 6/1992 | Chapman et al. |
| 5,135,527 A | 8/1992 | Ender |
| 5,167,666 A | 12/1992 | Mattheck et al. |
| 5,190,543 A | 3/1993 | Schlapfer |
| 5,197,966 A | 3/1993 | Sommerkamp |
| 5,201,735 A | 4/1993 | Chapman et al. |
| 5,211,645 A | 5/1993 | Baumgart et al. |
| 5,239,569 A | 8/1993 | Saleh et al. |
| 5,248,313 A | 9/1993 | Greene et al. |
| 5,263,955 A | 11/1993 | Baumgart et al. |
| 5,268,000 A | 12/1993 | Ottieri et al. |
| 5,281,224 A | 1/1994 | Faccioli et al. |
| 5,295,991 A | 3/1994 | Frigg |
| 5,334,192 A | 8/1994 | Behrens |
| 5,352,228 A | 10/1994 | Kummer et al. |
| 5,356,410 A | 10/1994 | Pennig |
| 5,397,328 A | 3/1995 | Behrens et al. |
| 5,403,321 A * | 4/1995 | DiMarco ............ A61B 17/1721 606/96 |
| 5,411,503 A | 5/1995 | Hollstien et al. |
| 5,415,660 A | 5/1995 | Campbell et al. |
| 5,429,638 A | 7/1995 | Muschler et al. |
| 5,433,718 A | 7/1995 | Brinker |
| 5,441,500 A | 8/1995 | Seidel et al. |
| 5,443,466 A | 8/1995 | Shah |
| 5,458,654 A | 10/1995 | Tepic |
| 5,472,444 A | 12/1995 | Huebner et al. |
| 5,484,438 A | 1/1996 | Pennig |
| 5,499,986 A | 3/1996 | Dimarco |
| 5,536,269 A | 7/1996 | Spievack |
| 5,549,610 A | 8/1996 | Russell et al. |
| 5,569,262 A | 10/1996 | Carney |
| 5,573,536 A | 11/1996 | Grosse et al. |
| 5,578,035 A | 11/1996 | Lin |
| 5,586,985 A | 12/1996 | Putnam et al. |
| 5,618,286 A | 4/1997 | Brinker |
| 5,620,445 A | 4/1997 | Brosnahan et al. |
| 5,620,449 A | 4/1997 | Faccioli et al. |
| 5,626,579 A | 5/1997 | Muschler et al. |
| 5,643,258 A | 7/1997 | Robioneck et al. |
| 5,645,545 A | 7/1997 | Bryant |
| 5,653,709 A | 8/1997 | Frigg |
| 5,658,283 A | 8/1997 | Huebner |
| 5,658,287 A | 8/1997 | Hofmann et al. |
| 5,665,086 A | 9/1997 | Itoman et al. |
| 5,681,318 A | 10/1997 | Pennig et al. |
| 5,690,634 A | 11/1997 | Muller et al. |
| 5,697,930 A | 12/1997 | Itoman et al. |
| 5,697,934 A | 12/1997 | Huebner |
| 5,713,902 A | 2/1998 | Friedl |
| 5,718,704 A | 2/1998 | Medoff |
| 5,766,174 A | 6/1998 | Perry |
| 5,766,179 A | 6/1998 | Faccioli et al. |
| 5,766,180 A | 6/1998 | Winquist |
| 5,776,194 A | 7/1998 | Mikol et al. |
| 5,779,705 A | 7/1998 | Matthews |
| 5,853,413 A | 12/1998 | Carter et al. |
| 5,928,235 A | 7/1999 | Friedl |
| 5,941,878 A | 8/1999 | Medoff |
| 5,954,722 A | 9/1999 | Bono |
| 5,961,553 A | 10/1999 | Coty et al. |
| 5,976,134 A | 11/1999 | Huebner |
| 5,997,490 A | 12/1999 | McLeod et al. |
| 6,010,505 A | 1/2000 | Asche et al. |
| 6,010,506 A | 1/2000 | Gosney et al. |
| 6,019,761 A | 2/2000 | Gustilo |
| 6,022,349 A | 2/2000 | McLeod et al. |
| 6,027,506 A | 2/2000 | Faccioli et al. |
| 6,033,407 A | 3/2000 | Behrens |
| 6,039,739 A | 3/2000 | Simon |
| 6,056,755 A | 5/2000 | Horas et al. |
| 6,074,392 A | 6/2000 | Durham |
| 6,077,264 A | 6/2000 | Chemello |
| 6,080,159 A | 6/2000 | Vichard |
| 6,093,192 A | 7/2000 | Abel |
| 6,096,040 A | 8/2000 | Esser |

(56) References Cited

U.S. PATENT DOCUMENTS

| | | |
|---|---|---|
| 6,120,504 A | 9/2000 | Brumback et al. |
| 6,123,708 A | 9/2000 | Kilpela et al. |
| 6,123,709 A | 9/2000 | Jones |
| 6,126,661 A | 10/2000 | Faccioli et al. |
| 6,146,384 A | 11/2000 | Lee et al. |
| 6,168,628 B1 | 1/2001 | Huebner |
| 6,200,321 B1 | 3/2001 | Orbay et al. |
| 6,206,880 B1 | 3/2001 | Karladani |
| 6,221,073 B1 | 4/2001 | Weiss et al. |
| 6,221,074 B1 | 4/2001 | Cole et al. |
| 6,224,601 B1 | 5/2001 | Friedl |
| 6,228,086 B1 | 5/2001 | Wahl et al. |
| 6,231,576 B1 * | 5/2001 | Frigg ............... A61B 17/7208 606/60 |
| 6,245,075 B1 | 6/2001 | Betz et al. |
| 6,248,109 B1 | 6/2001 | Stoffella |
| 6,261,289 B1 | 7/2001 | Levy |
| 6,270,499 B1 * | 8/2001 | Leu ............... A61B 17/72 606/62 |
| 6,273,892 B1 | 8/2001 | Orbay et al. |
| 6,283,969 B1 | 9/2001 | Grusin et al. |
| 6,296,645 B1 | 10/2001 | Hover et al. |
| 6,319,253 B1 | 11/2001 | Ackeret et al. |
| 6,355,069 B1 | 3/2002 | DeCarlo, Jr. et al. |
| 6,358,250 B1 | 3/2002 | Orbay |
| 6,364,882 B1 | 4/2002 | Orbay |
| 6,379,359 B1 | 4/2002 | Dahners |
| 6,379,360 B1 | 4/2002 | Ackeret et al. |
| 6,383,185 B1 | 5/2002 | Baumgart |
| 6,387,098 B1 | 5/2002 | Cole et al. |
| 6,395,033 B1 | 5/2002 | Pepper |
| 6,402,753 B1 | 6/2002 | Cole et al. |
| 6,409,768 B1 | 6/2002 | Tepic et al. |
| 6,416,516 B1 | 7/2002 | Stauch et al. |
| 6,423,066 B1 | 7/2002 | Harder et al. |
| 6,440,135 B2 | 8/2002 | Orbay et al. |
| 6,443,954 B1 | 9/2002 | Bramlet et al. |
| 6,461,360 B1 | 10/2002 | Adam |
| 6,488,684 B2 | 12/2002 | Bramlet et al. |
| 6,508,819 B1 | 1/2003 | Orbay |
| 6,508,820 B2 | 1/2003 | Bales |
| 6,514,253 B1 | 2/2003 | Yao |
| 6,524,313 B1 | 2/2003 | Fassier et al. |
| 6,524,314 B1 | 2/2003 | Dean et al. |
| 6,527,775 B1 * | 3/2003 | Warburton ............ A61B 17/164 606/62 |
| 6,533,788 B1 | 3/2003 | Orbay |
| 6,547,791 B1 | 4/2003 | Buhren et al. |
| 6,554,833 B2 | 4/2003 | Levy et al. |
| 6,572,620 B1 | 6/2003 | Schon et al. |
| 6,579,294 B1 | 6/2003 | Robioneck |
| 6,607,531 B2 | 8/2003 | Frigg |
| 6,629,976 B1 * | 10/2003 | Gnos ............... A61B 17/7291 606/62 |
| 6,648,889 B2 | 11/2003 | Bramlet et al. |
| 6,652,529 B2 | 11/2003 | Swanson |
| 6,656,189 B1 | 12/2003 | Wilson et al. |
| 6,658,189 B2 | 12/2003 | Ajima et al. |
| 6,660,009 B1 | 12/2003 | Azar |
| 6,702,816 B2 | 3/2004 | Buhler |
| 6,702,823 B2 | 3/2004 | Iaia |
| 6,706,046 B2 | 3/2004 | Orbay et al. |
| 6,709,436 B1 | 3/2004 | Hover et al. |
| 6,730,087 B1 | 5/2004 | Butsch |
| 6,730,090 B2 | 5/2004 | Orbay et al. |
| 6,736,818 B2 | 5/2004 | Perren et al. |
| 6,755,862 B2 | 6/2004 | Keynan |
| 6,767,351 B2 | 7/2004 | Orbay et al. |
| 6,786,908 B2 | 9/2004 | Hover et al. |
| 6,793,659 B2 | 9/2004 | Putnam |
| 6,796,984 B2 | 9/2004 | Soubeiran |
| 6,808,527 B2 | 10/2004 | Lower et al. |
| 6,866,665 B2 | 3/2005 | Orbay |
| 6,893,444 B2 | 5/2005 | Orbay |
| 6,926,720 B2 | 8/2005 | Castaneda |
| 7,018,380 B2 | 3/2006 | Cole |
| 7,033,365 B2 | 4/2006 | Powell et al. |
| 7,041,104 B1 | 5/2006 | Cole et al. |
| 7,160,302 B2 | 1/2007 | Warburton |
| 7,175,633 B2 | 2/2007 | Roth et al. |
| 7,247,156 B2 | 7/2007 | Ekholm et al. |
| 7,410,488 B2 | 8/2008 | Janna et al. |
| 7,455,673 B2 | 11/2008 | Gotfried |
| 7,588,577 B2 | 9/2009 | Fencl et al. |
| 8,303,590 B2 | 11/2012 | Elghazaly et al. |
| 8,771,283 B2 * | 7/2014 | Larsen ............... A61B 17/1725 606/96 |
| 2001/0011172 A1 | 8/2001 | Orbay et al. |
| 2002/0032446 A1 | 3/2002 | Orbay |
| 2002/0111629 A1 | 8/2002 | Phillips |
| 2002/0143337 A1 | 10/2002 | Orbay et al. |
| 2002/0143338 A1 | 10/2002 | Orbay et al. |
| 2002/0151897 A1 | 10/2002 | Zirkle, Jr. |
| 2002/0183753 A1 | 12/2002 | Manderson |
| 2003/0055428 A1 | 3/2003 | Swanson |
| 2003/0069581 A1 | 4/2003 | Stinson et al. |
| 2003/0073999 A1 | 4/2003 | Putnam |
| 2003/0083660 A1 | 5/2003 | Orbay |
| 2003/0083661 A1 * | 5/2003 | Orbay ............... A61B 17/8061 606/62 |
| 2003/0105461 A1 | 6/2003 | Putnam |
| 2004/0082955 A1 | 4/2004 | Zirkle, Jr. |
| 2004/0172026 A1 | 9/2004 | Ekholm et al. |
| 2005/0277936 A1 | 12/2005 | Siravo et al. |
| 2006/0015101 A1 * | 1/2006 | Warburton ......... A61B 17/1668 606/62 |
| 2006/0015123 A1 * | 1/2006 | Fencl ............... A61B 17/1659 606/104 |
| 2006/0064106 A1 | 3/2006 | Fernandez |
| 2006/0200141 A1 | 9/2006 | Janna et al. |
| 2006/0200143 A1 | 9/2006 | Warburton |
| 2006/0200144 A1 | 9/2006 | Warburton |
| 2006/0235394 A1 | 10/2006 | Martin |
| 2006/0241605 A1 | 10/2006 | Schlienger et al. |
| 2007/0016203 A1 | 1/2007 | Schlienger et al. |
| 2007/0049938 A1 | 3/2007 | Wallace et al. |
| 2007/0049940 A1 | 3/2007 | Wallace et al. |
| 2007/0123873 A1 | 5/2007 | Czartoski et al. |
| 2007/0123874 A1 | 5/2007 | Czartoski et al. |
| 2007/0123875 A1 | 5/2007 | Czartoski et al. |
| 2007/0123876 A1 | 5/2007 | Czartoski et al. |
| 2007/0123878 A1 | 5/2007 | Shaver et al. |
| 2007/0156144 A1 | 7/2007 | Ulrich et al. |
| 2007/0173835 A1 * | 7/2007 | Medoff ............... A61B 17/72 606/62 |
| 2007/0255283 A1 | 11/2007 | Ekholm et al. |
| 2007/0276382 A1 | 11/2007 | Mikhail et al. |
| 2007/0276385 A1 | 11/2007 | Schlienger et al. |
| 2007/0288017 A1 | 12/2007 | Kaup |
| 2007/0288019 A1 | 12/2007 | Schlienger et al. |
| 2008/0004623 A1 | 1/2008 | Ferrante et al. |
| 2008/0009869 A1 | 1/2008 | Schlienger et al. |
| 2008/0009873 A1 | 1/2008 | Yacoubian |
| 2008/0058813 A1 | 3/2008 | Gotfried |
| 2008/0091203 A1 | 4/2008 | Warburton et al. |
| 2008/0147066 A1 | 6/2008 | Longsworth et al. |
| 2008/0154264 A1 | 6/2008 | Wack et al. |
| 2008/0195098 A1 | 8/2008 | Gotfried |
| 2008/0208261 A1 | 8/2008 | Medoff |
| 2009/0157077 A1 | 6/2009 | Larsen et al. |
| 2009/0157079 A1 | 6/2009 | Warburton et al. |

FOREIGN PATENT DOCUMENTS

| | | |
|---|---|---|
| EP | 0 091 499 A1 | 10/1983 |
| EP | 0 118 778 | 9/1984 |
| EP | 0 355 411 | 7/1989 |
| EP | 0 491 138 B1 | 10/1991 |
| EP | 1 095 626 | 4/2000 |
| EP | 1 330 988 | 7/2003 |
| EP | 1 759 643 | 3/2007 |
| EP | 2 231 034 | 1/2013 |
| EP | 2 548 523 | 1/2013 |

(56) References Cited

FOREIGN PATENT DOCUMENTS

| | | |
|---|---|---|
| FR | 2 586 554 | 8/1985 |
| FR | 2 668 360 | 10/1990 |
| FR | 2 647 006 | 11/1990 |
| GB | 1 428 653 | 3/1976 |
| GB | 2 290 478 | 1/1996 |
| JP | 2 274 243 | 8/1990 |
| JP | 2001-286481 | 10/2001 |
| JP | 2002-528217 | 9/2002 |
| JP | 2011-506044 | 3/2011 |
| JP | 2013-223736 | 10/2013 |
| WO | WO 93/22978 | 11/1993 |
| WO | WO 98/18397 | 5/1998 |
| WO | WO 00/25681 | 5/2000 |
| WO | WO 01/56452 A3 | 1/2001 |
| WO | WO 03/037160 A2 | 5/2003 |
| WO | WO 2006/091625 | 8/2006 |
| WO | WO 2007/035772 | 3/2007 |
| WO | WO 2009/079503 | 6/2009 |

OTHER PUBLICATIONS

"The Alta Tibial/Humeral Rod Module for Reamed and Non-Reamed Procedures," Alta Modular Trauma System, (1992), 10 pages.
"Proximal Humeral Nailing System: Operative Technique," Stryker Corporation (2003), 20 pages.
"Intramedullary Fixation: Metaphysical/Diaphyseal Solutions," Zimmer, 6 pages (2000).
"Uniflex Humeral Nail System," Biomet Inc. (1991), 16 pages.
Nicholas J. Barton; "Smith's type I Fracture"; Fractures of the Hand and Wrist; 1988; p. 254; Churchill Livingstone.
Richard S. Smith, John C. Crick, Jorge Alonso, Marshall Horowitz, Open Reduction and Internal Fixation of Volar Lip Fractures of the Distal Radius, Journal of Orthopaedic Trauma, 1988, pp. 181-187, vol. 2 No. 3, Raven Press, Ltd., New York.
Jorge L. Orbay, Diego L. Fernandez, Volar Fixation for Dorsally Displaced Fractures of the Distal Radius: A Preliminary Report, The Journal of Hand Surgery, 2002, pp. 205-215, Miami, Florida.
Jorge L. Orbay, The Treatment of Unstable Distal Radius Fractures with Volar Fixation, Hand Surgery, Dec. 2000, pp. 103-112, vol. 5 No. 2, World Scientific Publishing Company.
Charles P. Melone, Jr., MD, Distal Radius Fractures: Patterns of Articular Fragmentation, Orthopedic Clinics of North America, Apr. 1993, pp. 239-253, vol. 24 No. 2.
"RAL Nail System: Titanium for Your Most Demanding Cases"; ACUMED 00674; 13 pages (date unknown, but thought to be before Sep. 2000 for the purposes of examination).
F. Fitoussi, W.Y. IP, S.P. Chow, Treatment of Displaced Intra-Articular Fractures of the Distal End of the Radius with Plates Article, JBJA Journal of Bone and Joint Surgery—American 1996-1998, Sep. 1997, 17 pgs., vol. 79-A, No. 9.
H. Drobetz, E. Kutscha-Lissberg, Osteosynthesis of distal radial fractures with a volar locking screw plate system, International Orthopaedics, Aug. 21, 2002, pp. 1-6, Springer-Verlag 2002.
Timothy A. Damron, MD, Peter J.L. Jebson, MD, Venkat K. Rao, MD, William D. Engber, MD, Mark A Norden, BS, Biomechanical Analysis of Dorsal Plate Fixation in Proximal Phalangeal Fractures, Annals of Plastic Surgery, Apr. 2, 1993, pp. 270-275, Little, Brown & Company.
"Intramedullary Nail for the Distal Radius," Aesculap Orthopaedics, Oct. 2006.
International Search Report and Written Opinion of the International Searching Authority for corresponding International Application No. PCT/US2008/086983 issued Mar. 3, 2009.
International Preliminary Report on Patentability for corresponding International Application No. PCT/US2008/086983 issued Jun. 22, 2010.
Office action issued May 13, 2014 in corresponding Japanese Patent Application No. 2013-113180.

* cited by examiner

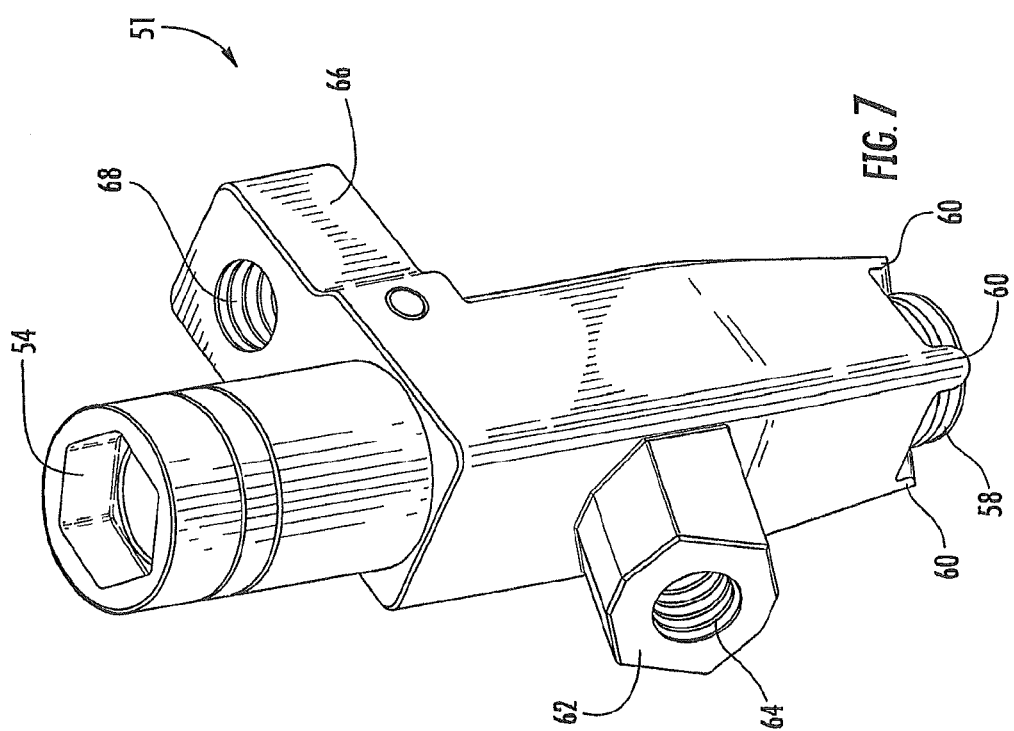

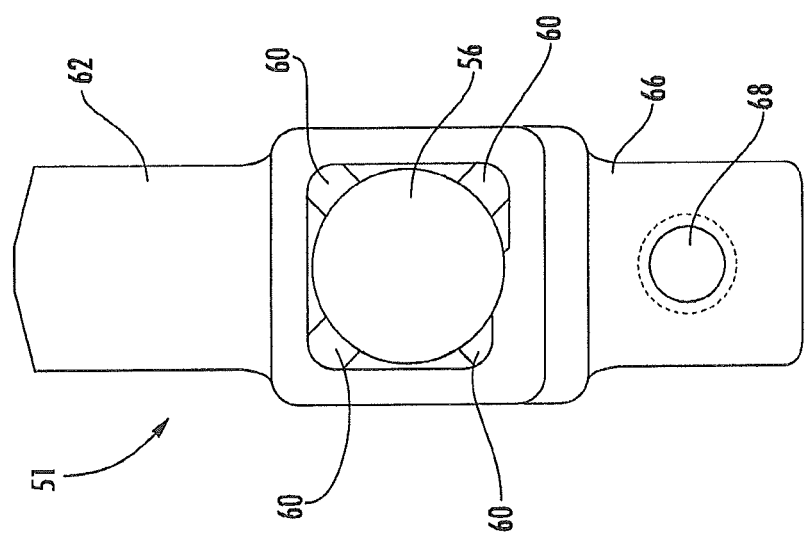

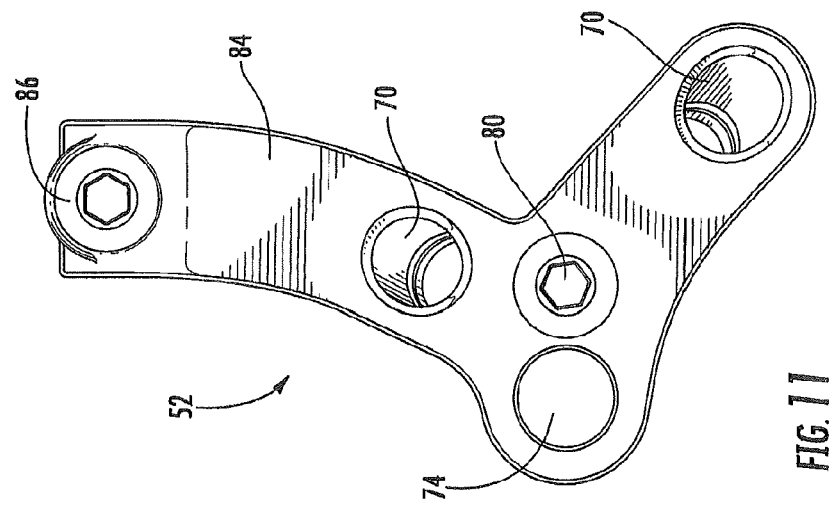
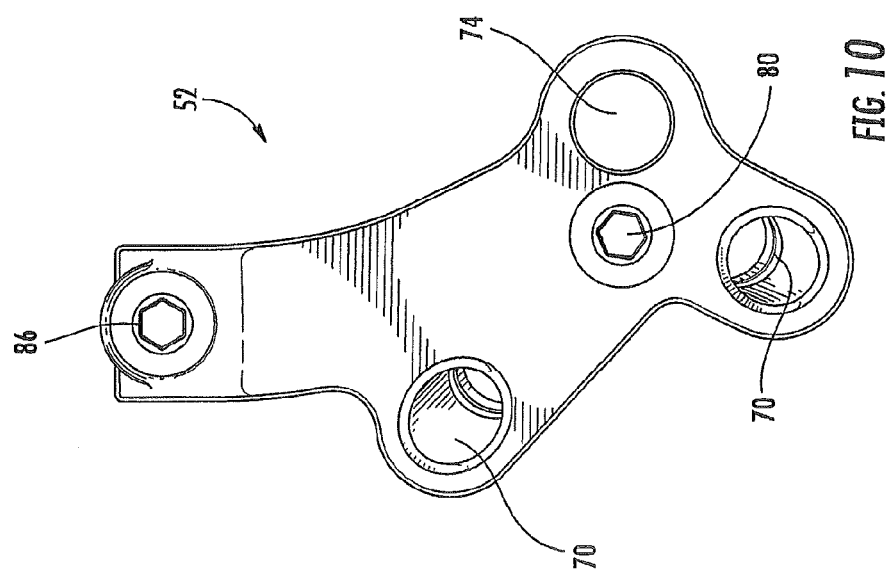

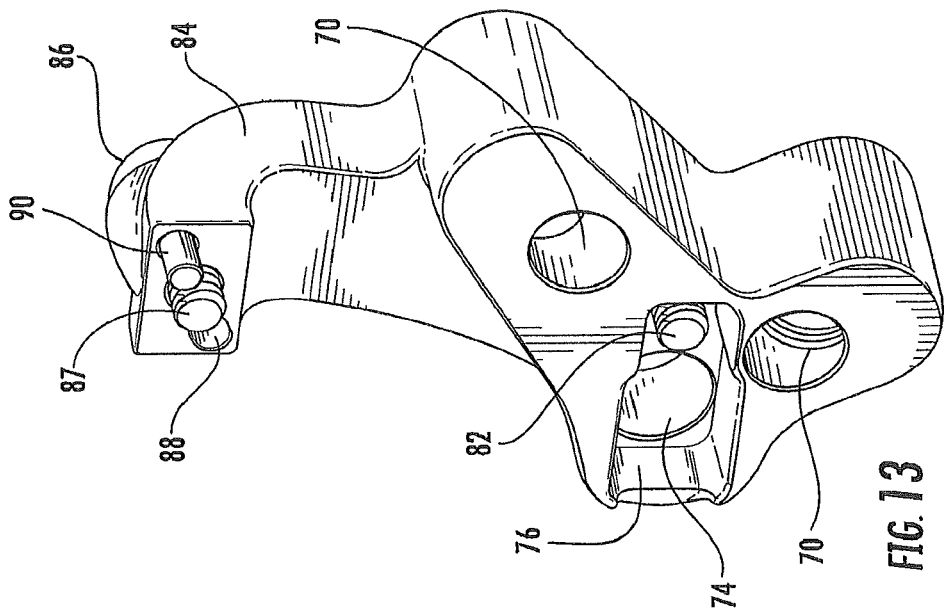
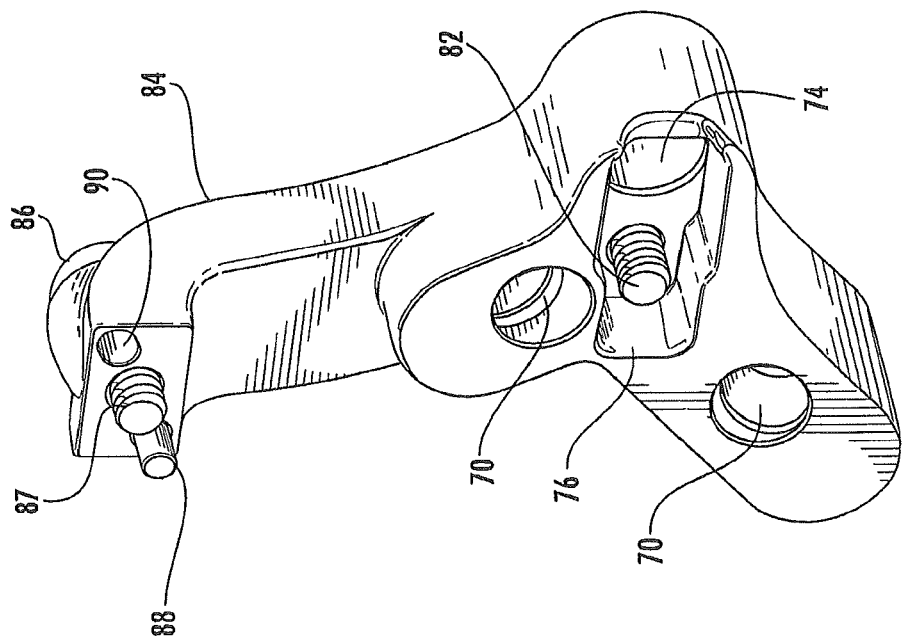

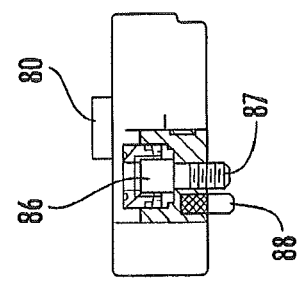
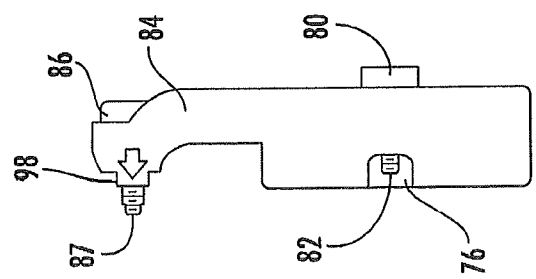
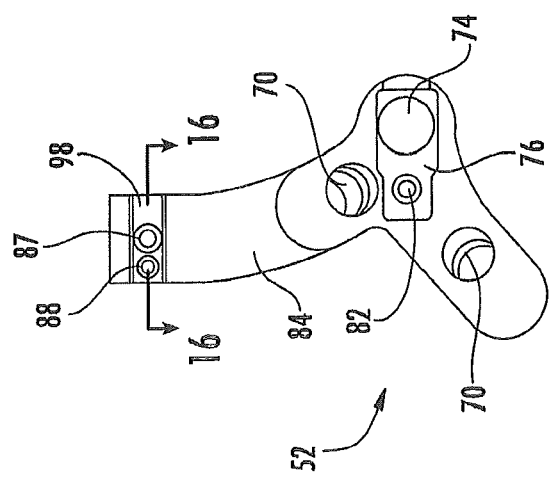

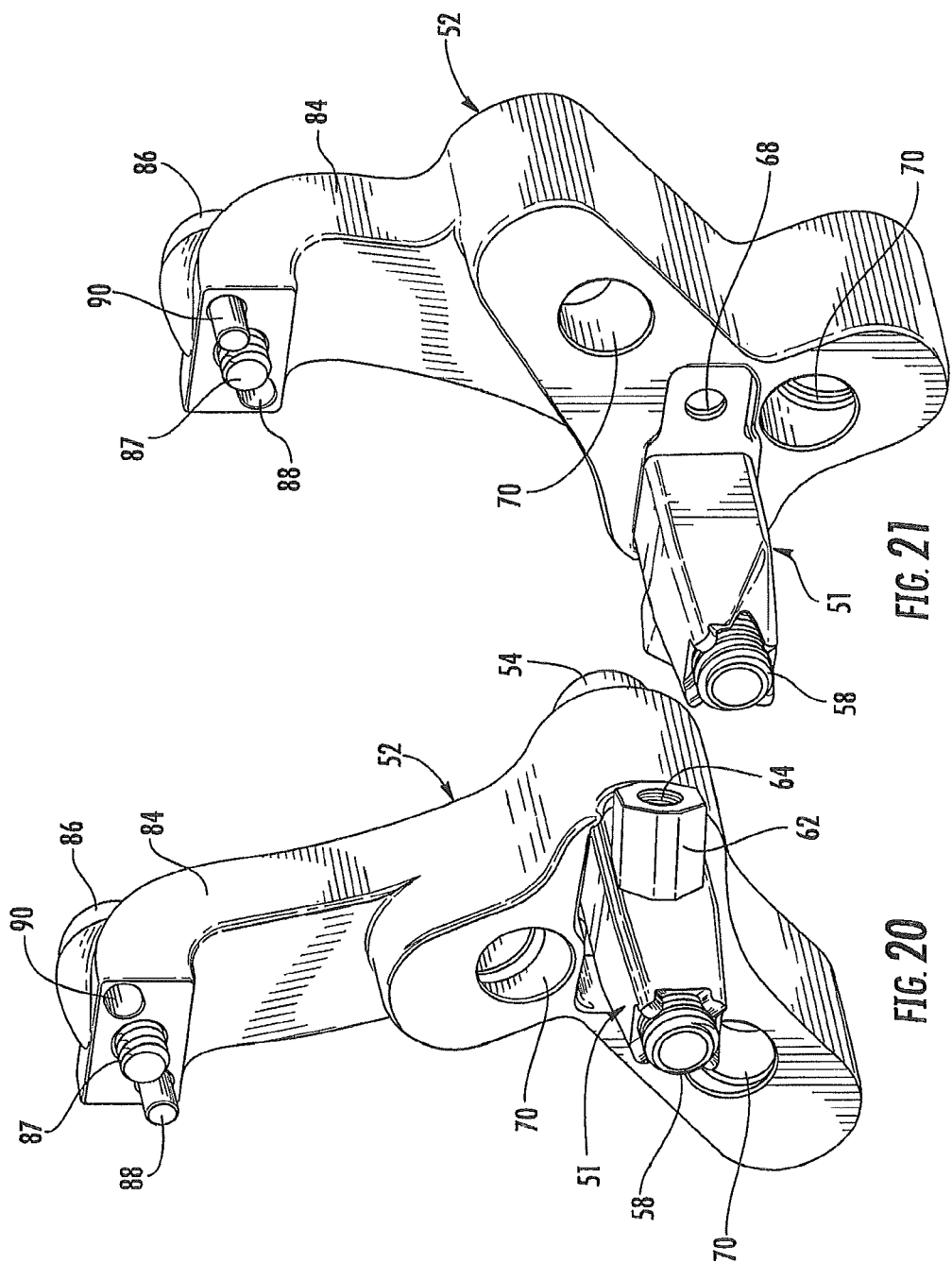

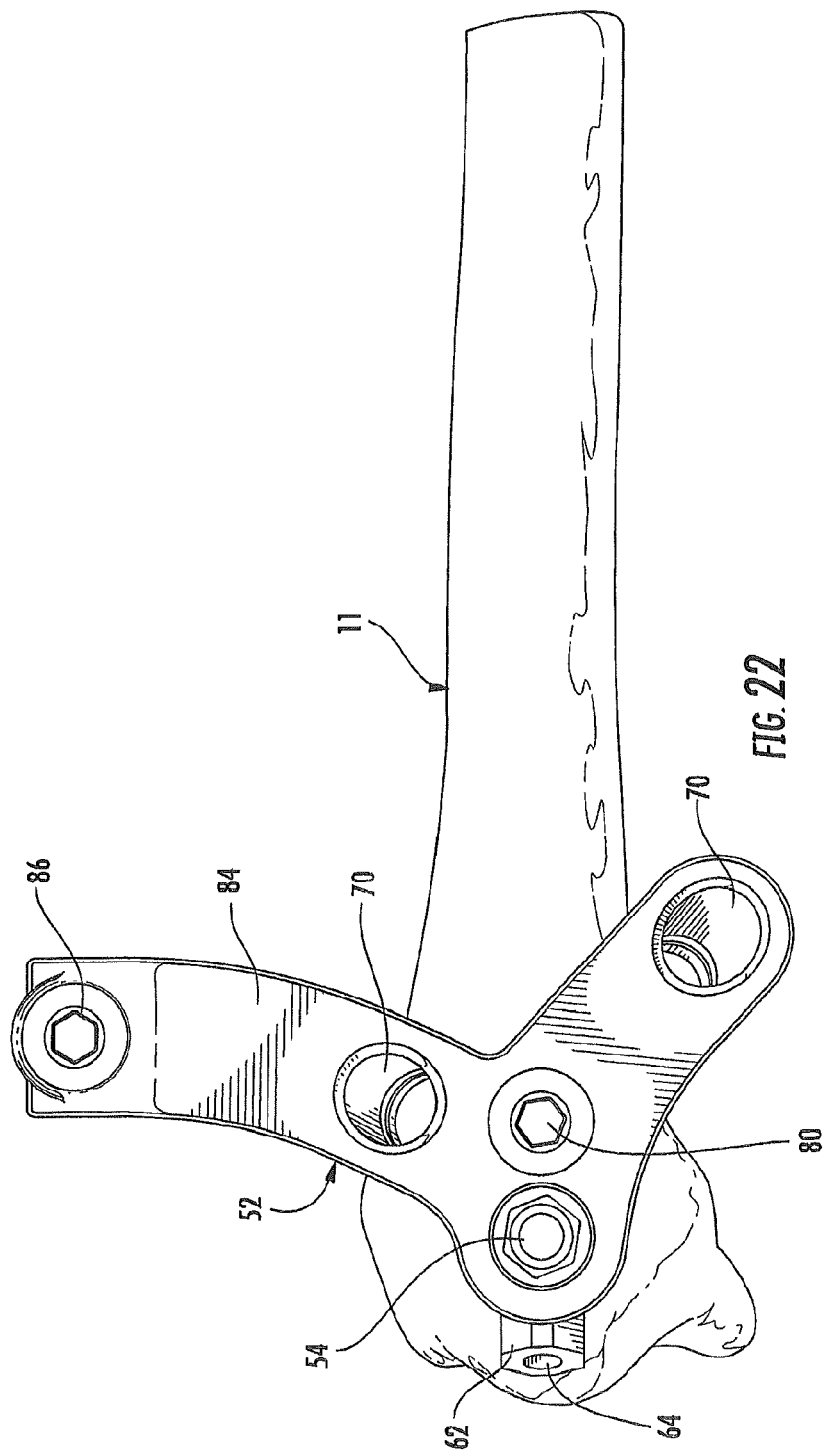

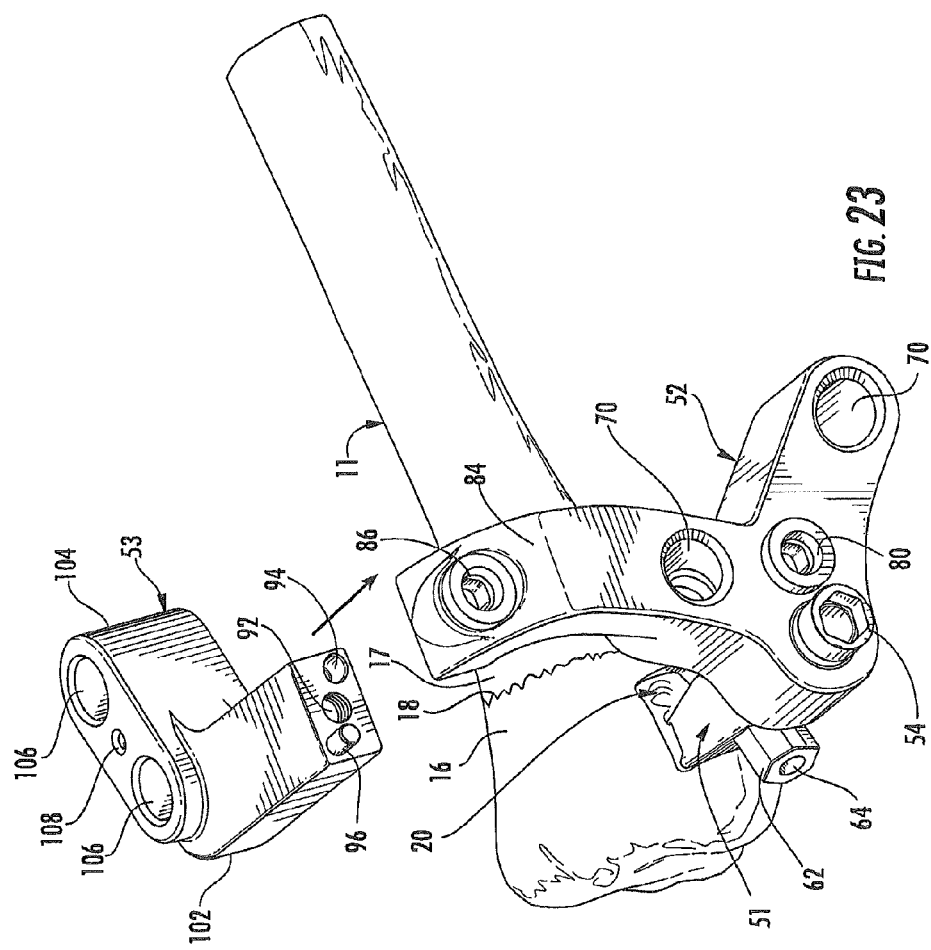

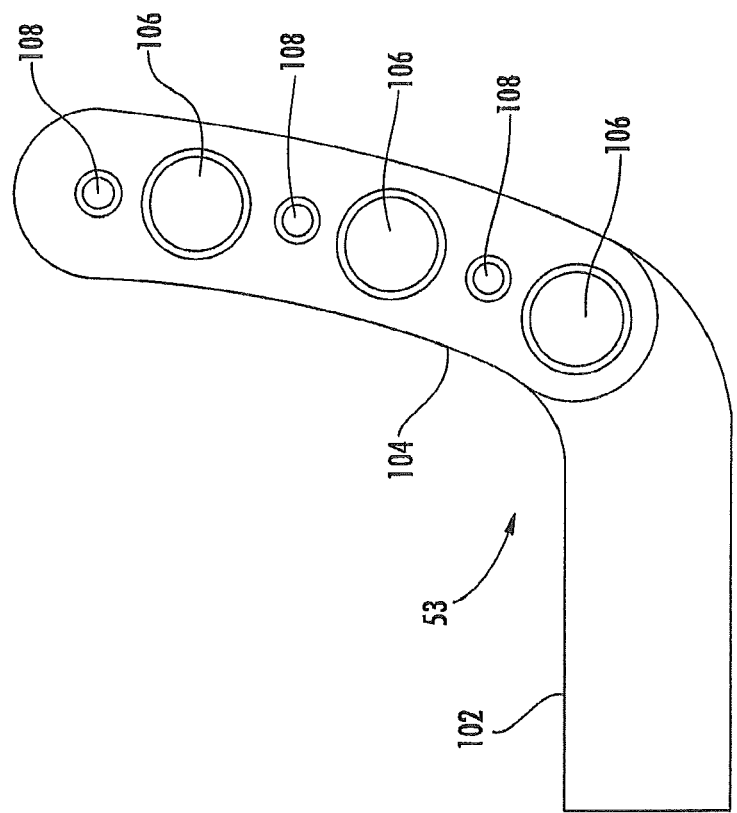

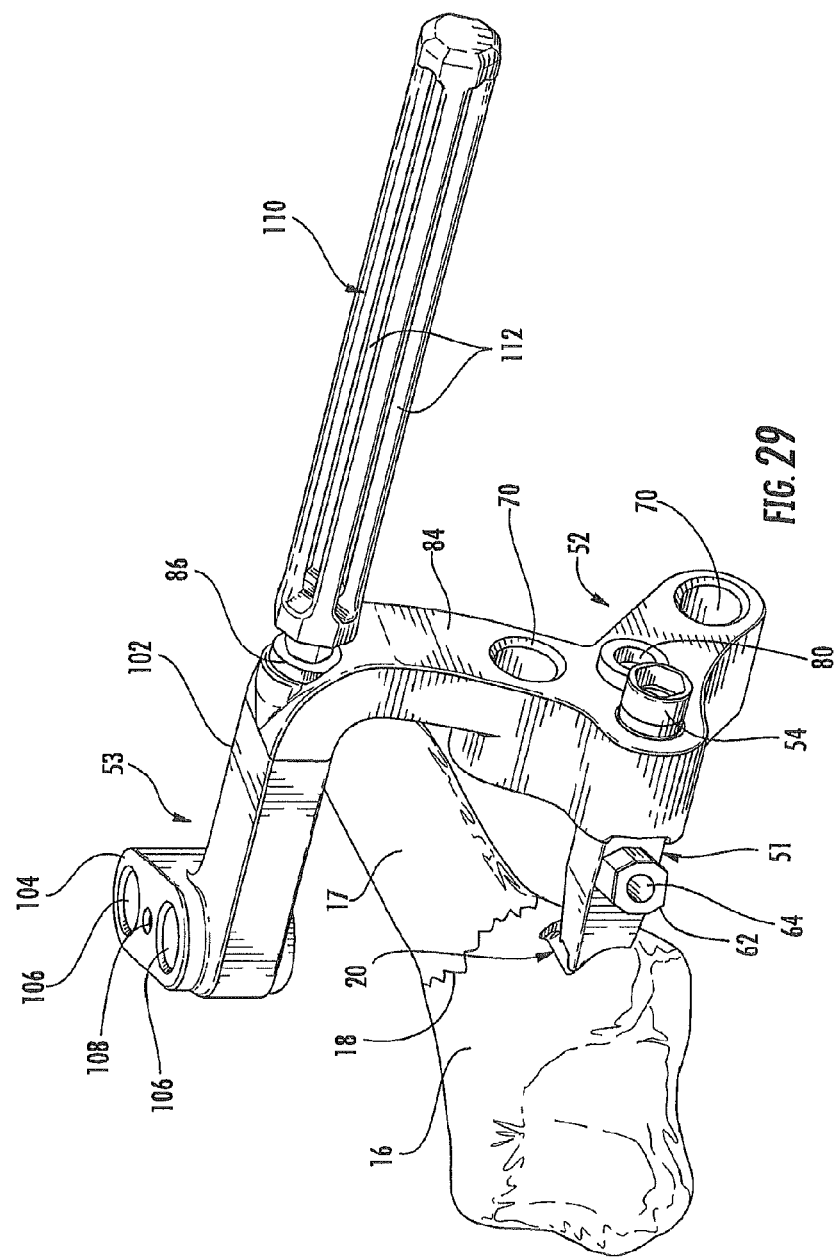

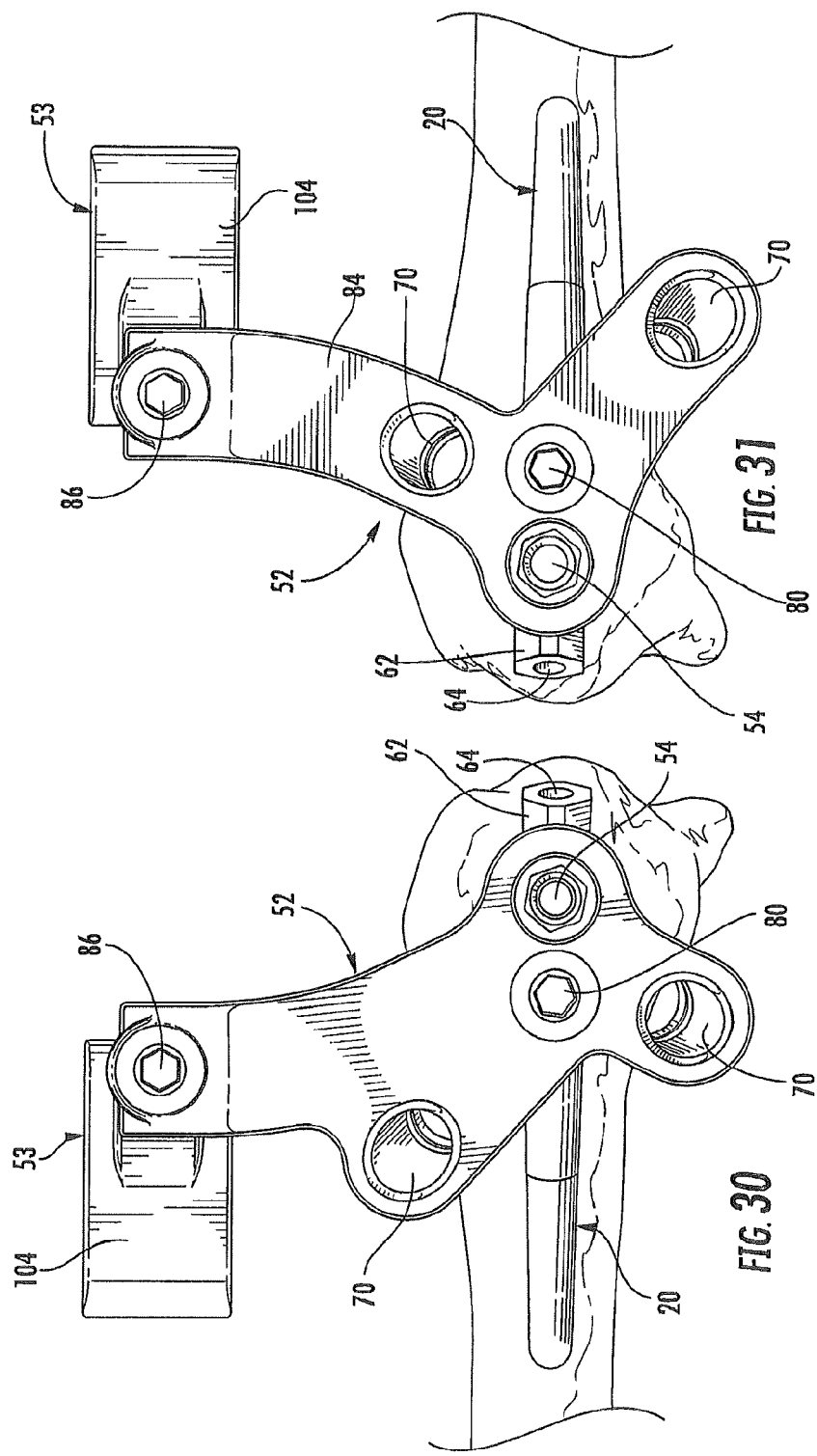

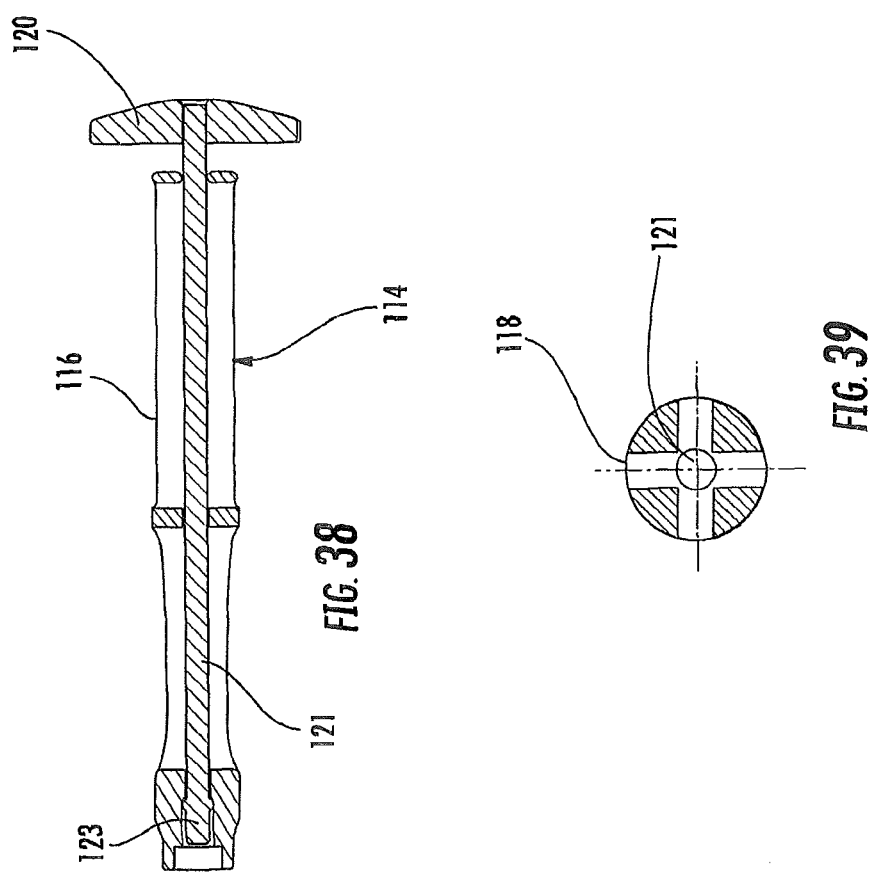

GUIDE ASSEMBLY FOR INTRAMEDULLARY FIXATION AND METHOD OF USING THE SAME

CROSS-REFERENCE TO RELATED APPLICATIONS

This application is a divisional of U.S. patent application Ser. No. 11/957,742, filed Dec. 17, 2007, which is incorporated herein by reference in its entirety.

BACKGROUND OF THE INVENTION

Field of the Invention

The present invention is related to the use of orthopedic fixation devices and devices for installing the same, and in particular, to intramedullary fixation devices and guides for facilitating installation and fixation of the same within the distal radius.

Description of Related Art

Long bone fractures are fairly common in the elderly population, often due to the onset of osteoporosis. Long bone fractures may be reduced by the use of assorted conventional bone plates. For example, a bone plate may be attached to the outside surface of two adjacent fragments of a long bone and then secured by inserting bone screws through openings in the bone plate. Problems may arise with such bone plates, however, in that the soft tissues covering the bone plates may become irritated by passage or movement over the bone plates.

An alternative to bone plates are intramedullary nails or rods that extend through a medullary canal defined within the fractured long bone. The nails or rods are typically fastened to the fractured portions of the long bones with bone screws. The nails or rods are placed into the medullary canal by insertion through a hole which is drilled into one end of the long bone. For instance, to reduce a fractured femur with an intramedullary rod or nail, a hole is drilled through the articular cartilage between the condyles to provide access for the rod. Because the intramedullary nails or rods are contained within the medullary canal, they avoid the problems with soft tissue associated with plates. However, insertion of these rods through holes in the ends of the longs bones requires damaging the articular cartilage on the ends of the long bones.

U.S. Pat. No. 6,527,775 to Warburton ("the '775 patent"), which is hereby incorporated herein in its entirety by reference, describes an intramedullary fixation device used to reduce a distal fracture of the radius. As shown in FIG. 3A of the '775 patent, the intramedullary fixation device 25 includes an elongated axially extending rod 26 with a distal portion 27 and a proximal portion 28. The fixation device also includes a distal fixation member 30 and proximal fixation members 35. The distal fixation member extends through the distal portion of the rod and into a distal fracture fragment 18. The proximal fixation members extend through the proximal portion of the rod and the portion of the radius proximal the fracture line.

Furthermore, the '775 patent discloses an insertion guide device 150 for guiding fixation members 35a, 35b into proximal fixation apertures $25a_1$, $25a_2$. The insertion guide device includes visual indicia 153, 155 that function as drill guides that align with the fixation apertures $25a_1$, $25a_2$. The insertion guide 150 attaches to a distal end portion 27 of the rod 26 and includes an axially extending arm residing external of the body. In addition, the insertion guide 150 is attached to the rod 26 prior to inserting the rod within the medullary canal.

Although the '775 patent discloses an insertion guide device for facilitating placement of the rod within the medullary canal, it would be advantageous to provide a guide assembly that facilitates easier placement of a fixation member within a radius. It would also be advantageous to provide a guide assembly that is capable of being easily assembled and disassembled and that provides a surgeon with more effective techniques for implanting a fixation member within a radius of a variety of patients.

BRIEF SUMMARY OF THE INVENTION

Embodiments of the present invention may address the above needs and achieve other advantages by providing a guide assembly for installing a fixation member within the medullary canal of the radius. The guide assembly generally provides an interchangeable guide assembly that allows the physician to more easily manipulate the fixation member, as well as adapt to patients of various sizes. The guide assembly may also comprise lighter and radiolucent material, which may also improve the installation process.

In one embodiment a guide assembly includes a guide fastener configured to attach to a fixation member and a guide member configured to receive the guide fastener such that the guide member is secured to the fixation member. The guide assembly also includes an interchangeable distal guide member configured to engage and be disengaged from the guide member. The distal guide member defines a plurality of fastener guide openings for guiding respective fasteners through a plurality of fastener openings defined in the fixation member.

According to various aspects of the guide assembly, the guide fastener is configured to engage an exposed proximal end of the fixation member that is accessible through a side aperture defined in the radius. The guide fastener may also include an opening configured to receive a drill guide therethrough. The guide member may define an opening configured to allow passage of the guide fastener through the guide member and into the exposed end of the fixation member. Moreover, the distal guide member may include an opening configured to align with the opening defined in the guide member and to allow passage of the guide fastener therethrough. The guide member may include a threaded opening for receiving a fastener to secure the proximal guide member to the guide member. In addition, the distal guide member may include a slot for engaging at least a portion of the guide member so as to prevent rotation of the guide member with respect to the distal guide member.

Additional aspects of the guide assembly include providing a handle that may attach to the guide member. The guide assembly may further include an interchangeable proximal guide member configured to engage and be disengaged from the distal guide member, wherein the proximal guide member defines a plurality of fastener guide openings for guiding respective fasteners into a plurality of fastener openings defined in the intramedullary fixation member that are located proximally of the plurality of fastener openings defined via the distal guide member. The distal guide member may include a protrusion, and the proximal guide member may include a channel for receiving the protrusion therein. The proximal guide member and distal guide member may be configured for threaded engagement. In addition, the distal guide member may include an alignment pin configured to engage an opening defined in the proximal guide member. The guide assembly may further include a plurality of tissue protectors, wherein each of the plurality of fastener guide openings of the proximal guide member and distal guide member may be configured to receive a respective tissue protector therethrough. The proximal and distal guide members are spaced outwardly from the radius such that the tissue protectors are configured to extend through the proximal guide member and distal guide member and adjacent to the radius. Moreover, the guide assembly may include a plurality of drill guides, wherein each of the plurality of tissue protectors is configured to receive a respective one of the drill guides therein.

An additional embodiment of the present invention provides an intramedullary fixation member kit for repairing a radius fracture. The kit includes an intramedullary fixation device configured to be positioned within an intramedullary canal of a radius and defining a plurality of fastener openings for receiving respective fasteners therethrough. The kit also includes a guide member configured to be coupled to the intramedullary fixation device and an interchangeable distal guide member configured to engage and be disengaged from the guide member. The distal guide member defines a plurality of fastener guide openings for guiding respective fasteners through a plurality of fastener openings defined in the intramedullary fixation member. The kit may also include an interchangeable proximal guide member and/or a guide fastener, as described above.

A further embodiment of the present invention relates to a method for placing a fixation member within a medullary canal of a radius. The method includes defining a side aperture in the radius that extends into a medullary canal thereof and attaching a guide member to the fixation member with a guide fastener. The method further includes inserting the fixation member through the side aperture until the fixation member is positioned in the medullary canal and side aperture and attaching an interchangeable distal guide member to the guide member, wherein the distal guide member defines a plurality of fastener guide openings. Moreover, the method includes defining a plurality of fastener openings within the radius via the plurality of fastener guide openings defined in the distal guide member that align with a plurality of fastener openings defined in the fixation member. The method also includes advancing a plurality of bone fasteners through the plurality of fastener guide openings defined in the distal guide member and the plurality of fastener openings defined in the fixation member and the radius.

Variations of the method include attaching an interchangeable proximal guide member to the distal guide member, wherein the proximal guide member defines a plurality of fastener guide openings. The method may further include defining a plurality of fastener openings within the radius via the plurality of fastener guide openings defined in the proximal guide member that align with a plurality of fastener openings defined in the fixation member that are located proximally of the plurality of fastener openings defined via the distal guide member. Furthermore, the method may include detaching the distal guide member from the guide member while the guide member is attached to the fixation member.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 7 is a perspective view of a guide member according to one embodiment of the present invention;

FIG. 8 is an end view of the guide member of FIG. 6;

FIG. 10 is an elevation view of a distal guide member according to one embodiment of the present invention;

FIG. 11 is an elevation view of a distal guide member according to an embodiment of the present invention;

FIG. 12 is a perspective view of distal guide member of FIG. 11;

FIG. 13 is a perspective view of distal guide member of FIG. 10;

FIGS. 14 and 15 are side elevation views of a distal guide member of another embodiment of the present invention;

FIG. 16 is a cross-sectional view of the distal guide member of FIG. 14;

FIG. 20 is perspective view of a guide member coupled to a distal guide member according to one embodiment of the present invention;

FIG. 21 is perspective view of a guide member coupled to a distal guide member according to an embodiment of the present invention;

FIG. 22 is a side elevation view of a distal guide member coupled to a radius according to one embodiment of the present invention;

FIG. 23 is a side elevation view of a guide member coupled to radius, a distal guide member coupled to the guide member, and a proximal guide member prior to engaging the distal guide member, according to one embodiment of the present invention;

FIG. 28 is a side elevation view of a proximal guide member according to another embodiment of the present invention;

FIG. 29 is a perspective view of a guide member coupled to a distal radius, a distal guide member coupled to the guide member, and the distal guide member coupled to a proximal guide member, according to one embodiment of the present invention;

FIGS. 30 and 31 are side elevation views of a guide member coupled to a distal radius, a distal guide member coupled to the guide member, and the distal guide member coupled to a proximal guide member, according to one embodiment of the present invention;

FIGS. 38 and 39 are cross-sectional views of a handle according to one embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
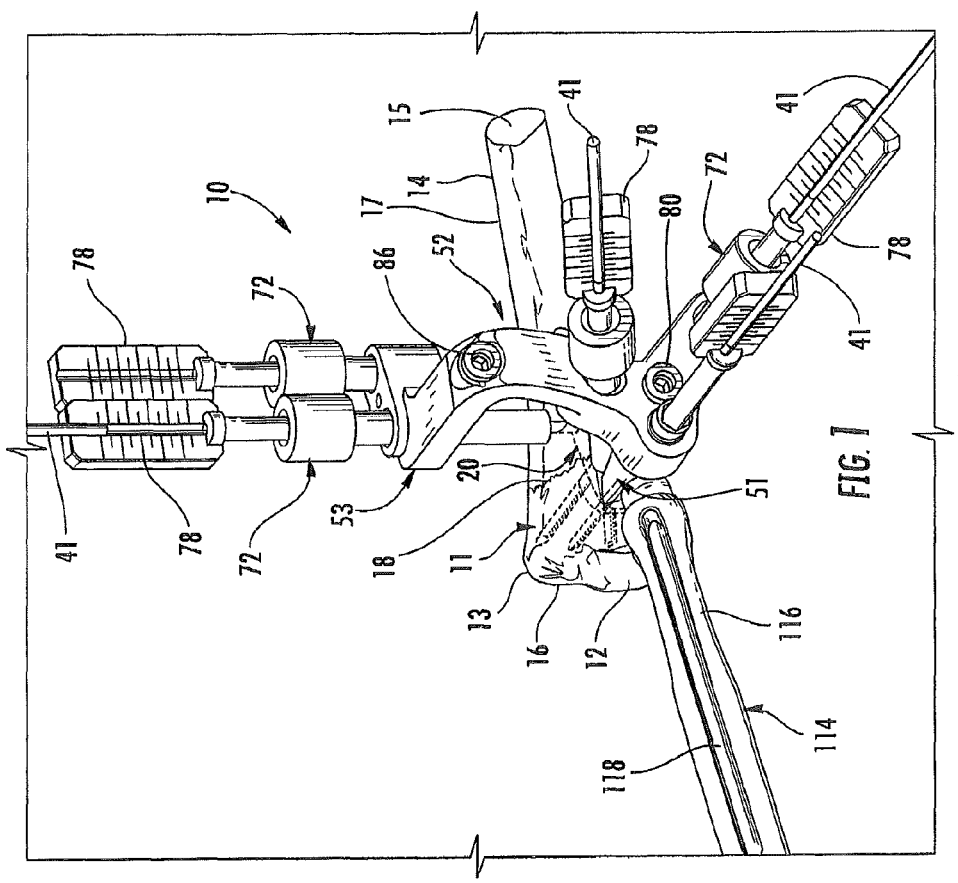
FIG. 1 is a perspective view of a guide assembly coupled to a fixation member according to one embodiment of the present invention.

A guide assembly 10 of one embodiment of the present invention is shown coupled to a radius 11 of a patient in FIG. 1. The guide assembly 10 is employed to install a fixation member 20 within the radius 11, as explained in further detail below. The fixation member 20 is most suited for repairing fractures of the distal radius 11 wherein the fracture is at one end near an articular cartilage surface 12 and wherein it is desired to leave the articular surface undisrupted during the repair. Although reference is made herein to a guide assembly 10 and fixation member 20 suitable for the radius, it is understood that the guide assembly may be configured to install a fixation member in a variety of long bones, such as a femur, tibia, radius or humerus.

Figure 2:
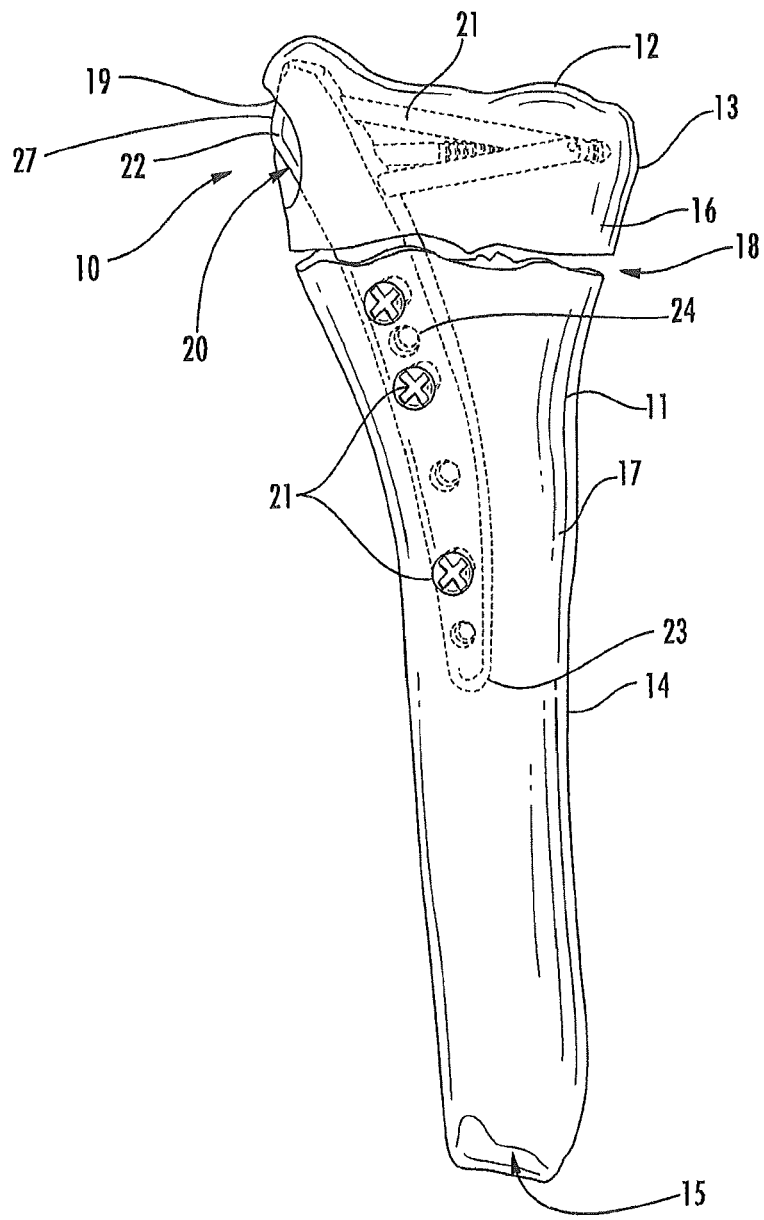
FIG. 2 is a side elevation view of a fixation member positioned within the medullary canal of a radius according to one embodiment of the present invention.

As shown in FIG. 2, the radius 11 generally includes a widened end 13 that supports the articular cartilage surface which tapers to a more narrow shaft 14. Extending within the shaft 14 and a portion of the widened end 13 is a medullary canal 15. In addition, the guide assembly 10 and fixation member 20 could be used to repair a variety of fractures of the long bones, but is shown being used to repair a first bone fragment 16 separated from a second bone fragment 17 by a single fracture line 18. A side aperture 19 is defined in a lateral surface of the widened end 13, subjacent the articular cartilage surface 12, to allow insertion of the fixation member 20.

Generally, the fixation member 20 is configured to receive a plurality of fasteners 21 therethrough and attach to the radius 11 above and below the fracture line 18 and thereby reduce the fracture, for example, as shown in FIG. 2. The elongate fixation member 20, when positioned within the medullary canal 15 of the radius 11, has a first end 22 positioned adjacent the side aperture 19. Extending from the first end, through the rest of the aperture and into the medullary canal 15 of the first bone fragment 16, is a curved body 24 (shown in broken lines in FIG. 2) of the fixation member 20. The curved body 24 extends to a second end 23 which is positioned within the medullary canal 15 of the second bone fragment 17. Advantageously, a radius of curvature of the curved body 24 is selected to promote smooth insertion of the curved body through the side aperture 19 and into the medullary canal 15.

Figure 3:
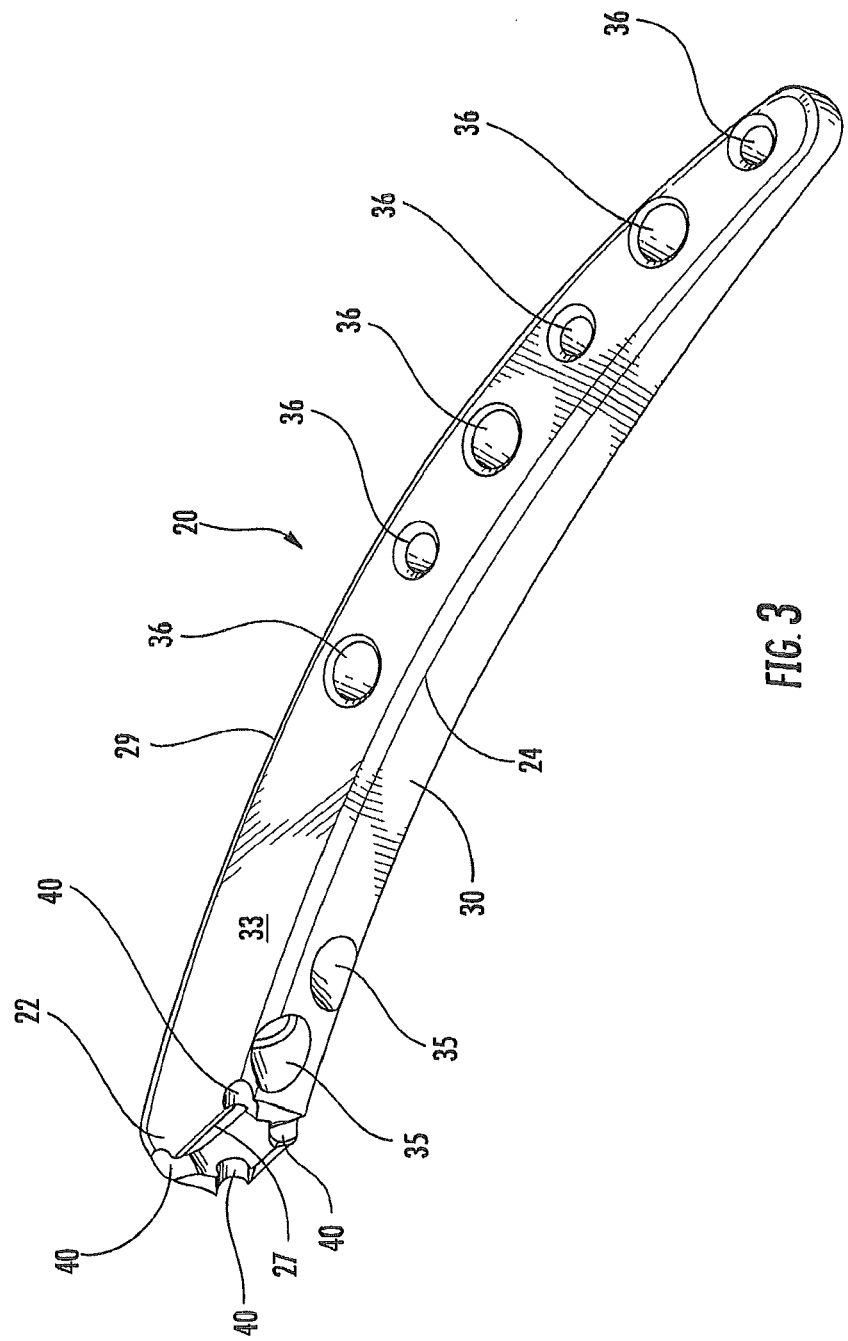
FIG. 3 is a perspective view of the fixation member of FIG. 1.
Figure 4:
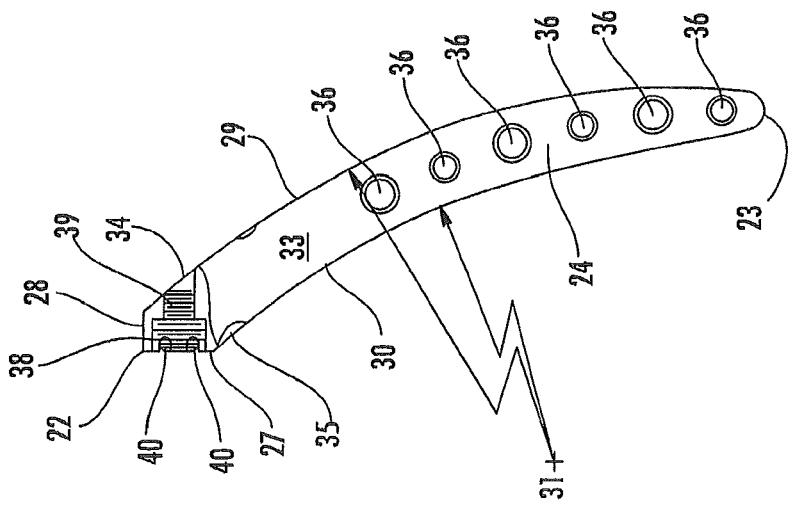

For example, one embodiment of the fixation member 20 of the present invention is shown in FIGS. 3-6. The first end 22 of the fixation member 20 has two intersecting flat surfaces, including an exposed first end surface 27 that is accessible through the side aperture 19 and an adjacent first end surface 28 that is at a right angle to the exposed surface, as shown in FIG. 4. The second end 23 of the fixation member 20 may have a rounded profile.

The curved body 24 of the fixation member 20 includes a convex side 29 and a concave side 30 that are on opposite sides of the curved body. The sides have radii of curvature with a similar center, but the center of the convex side changes so that the sides converge in a slight taper as they extend to the second end 23, as shown in FIG. 4. For instance, the radius of curvature of the concave side 30 is about 3.12 inches and the radius of curvature of the convex side 29 is about 3.40 inches near the first end 22 when measured from a first center 31 positioned about 2.31 inches from the plane of the adjacent first end surface 28 and about 2.35 inches from the plane of the exposed first end surface 27. Notably, this shift produces the taper near the second end 23 of the fixation member 20.

Figure 6:
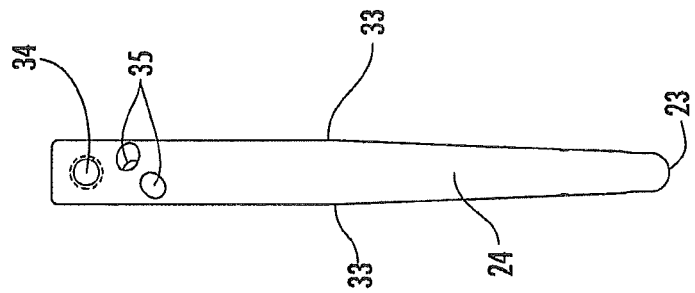
FIGS. 4-6 are side elevation views of the fixation member of FIG. 3.
Figure 5:
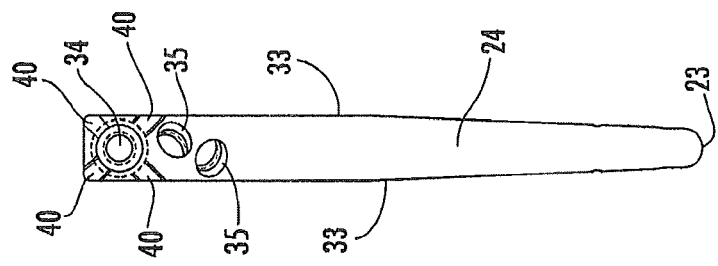

A second pair of opposite, side surfaces 33 extend between the convex side 29 and concave side 30, as shown in FIGS. 3, 5, and 6. Similar to the convex side 29 and concave side 30, the side surfaces 33 taper slightly toward each other as they extend from the first end 22 to the second end 23 of the curved body 24. However, the side surfaces 33 in the illustrated embodiment are relatively planar, as opposed to the curved shape of the sides 29, 30. Advantageously, the taper of the sides 29, 30, 33, the continuous curve of the curved body 24 between the ends 22, 23 and the rounded profile of the second end 23 help to facilitate insertion through the side aperture 19 and into the medullary canal 15.

To allow passage of the fasteners 21 through the fixation member, a plurality of fastener openings are defined in the fixation member. These fastener openings include a side aperture accessible fastener opening 34, a pair of fastener openings 35 extending between the curved convex side 29 and concave side 30, and fastener openings 36 extending between the side surfaces 33. The fastener opening 34 extends from the exposed first end surface 27 (which is accessible through the side aperture 19 when the fixation member 20 is installed) through a portion of the curved body 24 and to the convex side 29, as shown in FIG. 4. The fastener opening 34 includes a guide portion 38 and a fastener portion 39 that is generally narrower than the guide portion. Both of the portions may be threaded to facilitate a secure fit by the fasteners 21 and various installation devices, as will be described in more detail below. Defined around the periphery of the guide portion 38 of the fastener opening 34 are four indentations 40. These indentations 40 are arranged in a cross, or cruciform, shape each radiating out from the fastener opening 34 and spaced 90° from each other. As will be described in more detail below, the concave indentations 40 serve to provide for a secure, properly oriented positive fit with a guide assembly 10.

The pair of fastener openings 35 which extend between the sides 29, 30 extend through the curved body 24 nearer the first end 22 so as to be within the first bone fragment 16, as shown in FIGS. 2, 5, and 6. Each of the fastener openings 35 may have a threaded fastener portion similar to the fastener opening 34, but a non-threaded fastener head portion which may define a counterbore. These fastener openings 35 extend at different, divergent angles than each other and the orientation of the fastener opening 34 which is relatively orthogonal with respect to the exposed first end surface 27 and the convex side 29, as shown in FIGS. 3, 5, and 6. As a result, the fastener openings (such as the fastener openings 35) need not all be aligned with the axis of the fixation member.

These different angles improve fixation by allowing angled insertion of the fasteners 21 into different portions of the first bone fragment 16, as shown in FIG. 2. In addition, the angles of the fastener openings 34, 35 may be configured so that the fasteners extend subjacent to the articular cartilage for improved fixation. Generally, this will require the fastener openings 34, 35 to extend at some acute angle, such as an angle between about 50° and 85° (depending on the origin of the fastener opening), and preferably about 60° to 70°, with respect to the fixation member 20. Basically, these angles are to match the inclination angle of the articular surface so as to provide a buttress effect for the articular cartilage. For instance, the ulnar inclination angle of the articular cartilage on the radius is about 23° (resulting in a 67° fastener opening angle). The buttress effect is also improved by the sub-chondral placement of the first end surface 28 that is adjacent and at a right angle with respect to the exposed first end surface 27 so as to underlie the articular cartilage.

In the illustrated embodiment shown in FIGS. 3 and 4, six fastener openings 36 are defined in the curved body 24 at a position nearer the second end 23 of the fixation member 20. The fastener openings 36 having the larger diameter are configured to receive threaded fasteners 21 therethrough, similar to the fastener openings 34, 35, while the fastener openings having a smaller diameter are configured to receive a relatively smaller diameter Kirschner wire/k-wire 41. The larger of the fastener openings 36 may not be threaded to allow a slip fit of the threaded fasteners 21 through the fixation member 20 without damaging the threads. Furthermore, FIG. 2 demonstrates that the fixation member 20 may be positioned within the radius 11 such that each of the larger fastener openings 36 may guide respective fasteners 21 in the second bone fragment 17.

Although six fastener openings are shown in the illustrated fixation member 20, it is understood that the fixation member may include any number of desired fastener openings. For example, the fixation member 20 may be configured to be a size 1 or 2 implant such that increasing to a size 3 or 4 implant may include additional fastener openings 35 and/or 36. Moreover, it is understood that the fixation member 20 could be a variety of configurations depending on the type of long bone, the patient, and/or other factors. For additional details regarding a fixation member and bone fasteners according to additional embodiments of the present invention, Applicants hereby incorporate by reference U.S. Patent Appl. Publ. No. 2006/0015101, filed Jul. 15, 2004, herein in its entirety.

FIG. 1 illustrates a guide assembly 10 according to one embodiment of the present invention. The guide assembly generally includes a guide member 51, a distal guide member 52, and a proximal guide member 53. As discussed in detail below, the guide member 51 and distal 52 and proximal 53 guide members are capable of being engaged to and disengaged from each other so as to provide an interchangeable guide assembly 10 that may provide for easier installation of the fixation member 20 within the radius 11.

Figure 9:
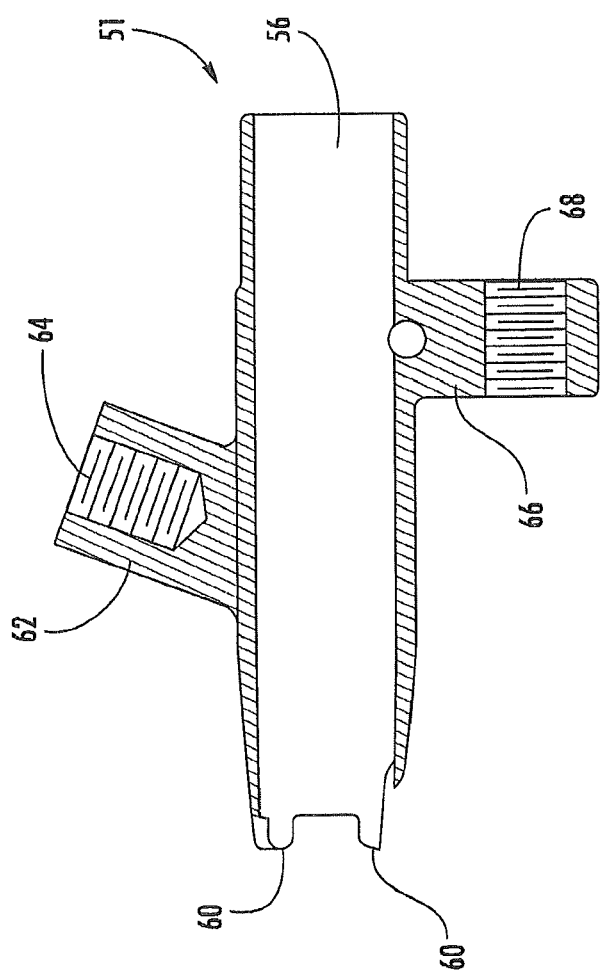
FIG. 9 is a cross-sectional view of the guide member of FIG. 6.

FIGS. 7-9 illustrate a guide member 51 according to one embodiment of the present invention. The guide member 51 is configured to be coupled to the distal end of the fixation member 20 via a guide fastener 54. In particular, the guide member 51 includes a longitudinal opening 56 that is configured to receive the guide fastener 54 therethrough. The guide fastener 54 includes a threaded end 58 that is configured to mate with threads defined in the fastener opening 34 of the fixation member 20. Moreover, the guide member 51 includes a plurality of prongs 60 that are configured to fit into similarly shaped, but somewhat smaller, concave indentations 40 in a positive, or interference, type fit, as shown, for example, in FIG. 33.

When the threaded end 58 is advanced into the threads of the guide portion 38, the guide member 51 and its prongs 60, which are also spaced in a cruciform or cross pattern similar to the indentations 40, are advanced into the indentations. The cruciform pattern, combined with the positive fit, firmly locks the guide member 51 to the fixation member 20 before attaching the distal 52 and proximal 53 guide members, as well as during guidance of insertion of the various fasteners 21. The cruciform shape and positive fit may be effective at restricting rotation between the guide assembly 10 and fixation member 20, which can be a problem due to the relative length and cantilevered configuration of the guide assembly and fixation member. It should be noted, however, that the positive fit of the prongs 60 in the concave indentations 40 could be accomplished in other ways, such as by having the indentations on the guide member 51 instead of the exposed first end surface 27 of the fixation member 20.

The guide member 51 also includes a handle mount 62 and a threaded opening 64 extending therethrough that is configured to mate with a handle 114, as shown in FIGS. 32-34, 36, and 37. The handle 114 is typically used to manipulate the fixation member 20 within the medullary canal 15, as explained in additional detail below. Moreover, the guide member 51 includes a protrusion 66 that also includes a threaded opening 68. As also explained in further detail below, the protrusion is configured to mate with a slot 76 defined in the distal guide member 52. The protrusion 66 is shown as being generally rectangular, but could be various sizes and configurations to mate with the slot 76 of the distal guide member 52, such as tapered to engage a tapered slot in an interference type of fit.

FIGS. 10-13 illustrate distal guide members 52 according to particular embodiments of the present invention. The distal guide member 52 shown in FIGS. 10-13 may be used for guiding fasteners 21 within the first end 22 of the fixation member 20 and the first bone fragment 16. In particular, the distal guide member 52 shown in FIGS. 10 and 13 may be configured to guide fasteners 21 within the patient's left radius 11, while the distal guide member 52 shown in FIGS. 11 and 12 may be used to guide fasteners in the right radius.

Each of the distal guide members 52 shown in FIGS. 10-13 includes a plurality of openings 70. The openings 70 are oriented so as to have an axis collinear and aligned with the axes of the pair of openings 35 defined in the curved body 24 of the fixation member 20. According to one embodiment, the openings 70 are defined so that the fasteners 21 extend at an angle into the first bone fragment 16 below the articular cartilage surface 12, as shown in FIG. 2.

Figure 34:
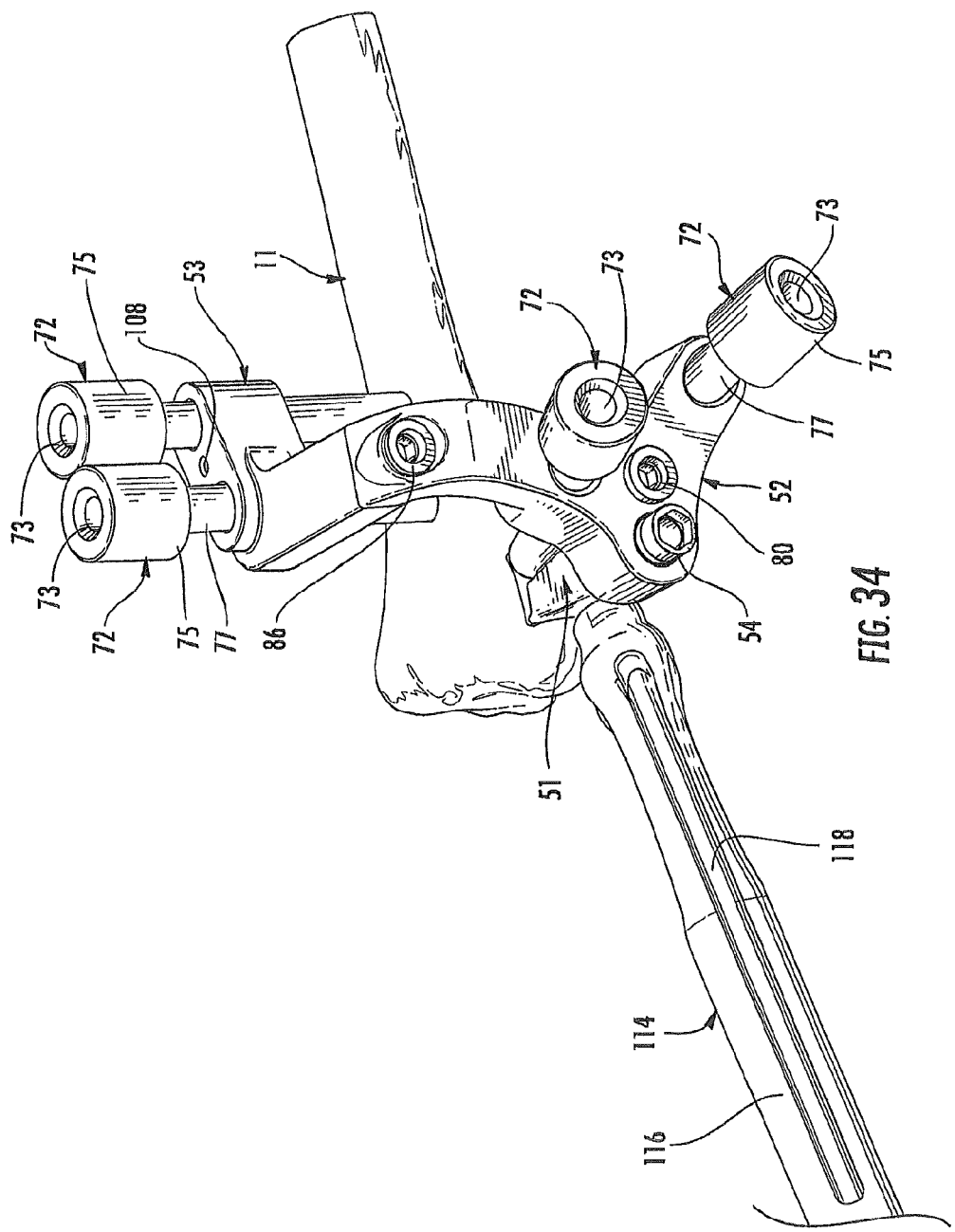
FIG. 34 is a perspective view of a guide assembly of FIGS. 32 and 33 coupled to the radius and tissue protectors positioned within the proximal and distal guide members according to one embodiment of the present invention.

Furthermore, the openings 70 are configured to slidably receive respective tissue protectors 72 therethrough, as shown in FIG. 34. Each tissue protector 72 includes a head 75 and a longitudinal shaft 77, wherein the shaft is configured to extend through the openings 70 and adjacent to the radius. Thus, the distal end of the tissue protector is capable of being inserted through the skin and abutting the radius. The offset distance between the distal guide member 52 and the patient's skin may allow the distal guide member 52 to accommodate patients of a variety of sizes, while the tissue protectors 72 may protect the patient's skin from injury resulting from implanting the fixation member 20, such as from drilling into the tissue. Furthermore, the distal guide members 52 include an opening 74 configured to receive the guide fastener 54 therethrough, as shown in FIGS. 20 and 21. FIGS. 1 and 34 show that the tissue protectors 72 and guide fastener 54 include respective longitudinal openings 73 that are configured to receive drill bits, k-wires, drill guides, fasteners, and the like in order to facilitate placement of the fixation member 20 within the radius 11. For example, FIG. 1 shows each of the tissue protectors 72 and guide fastener 54 may have a drill guide 78 positioned therein.

Each distal guide member 52 also includes a slot 76 that is configured to mate with the protrusion 66 of the guide member 51. Extending within the slot 76 is a fastener 80 having a threaded end 82 that is configured to engage with the threads 68 of the protrusion 66. The engagement of the protrusion 66 and fastener 80 within the slot 76 provides resistance to rotational movement between the guide member 51 and the distal guide member 52, which may ensure more accurate placement of fasteners 21 within the radius 11. The slot 76 is generally rectangular in configuration but could be modified to a variety of sizes and configurations to mate with the protrusion 66 and resist rotational movement therebetween.

Each distal guide member 52 shown in FIGS. 10-13 includes a hook-shaped portion 84 that includes a curvature that is configured to extend partially about the circumference of the patient's wrist and engage a proximal guide member 53. The distal guide members 52 of FIGS. 10-13 include a fastener 86 and an associated threaded end 87 that is configured to thread an opening 92 defined in the proximal guide member 53, as shown in FIG. 23. However, it is understood that the proximal guide member 53 may include a fastener that is configured to engage threads defined in the distal guide member 52 such that the proximal and distal guide members are threadably engageable with one another. In addition, the distal guide members 52 of FIGS. 10-13 include an alignment pin 88 configured to engage an opening 94 defined in the proximal guide member 53, while the proximal guide member 53 may also include an alignment pin 96 that is configured to engage an opening 90 defined in the distal guide member 52. Thus, the combination of alignment pins and threaded engagement between the distal 52 and proximal 53 guide members provides a secure attachment, while also providing the surgeon with the option of removing the distal guide member, such as to replace the distal guide member with a different size.

Figure 19:
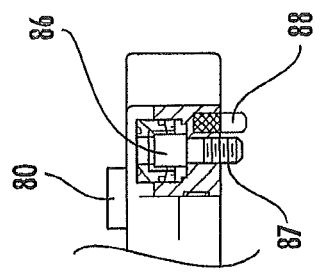
FIG. 19 is a cross-sectional view of the distal guide member of FIG. 17.
Figure 18:
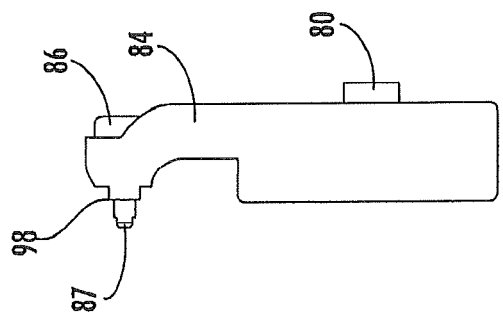
FIGS. 17 and 18 are side elevation views of a distal guide member of one embodiment of the present invention.
Figure 17:
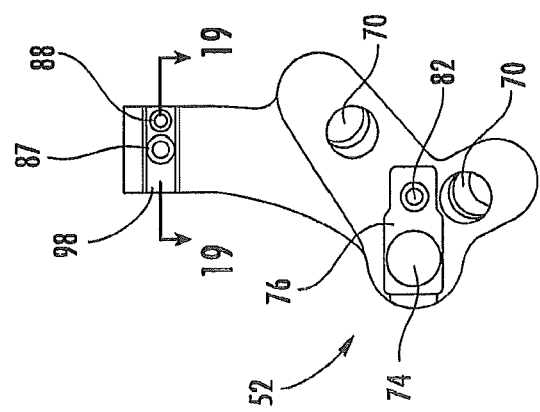

FIGS. 14-19 illustrate additional embodiments of a distal guide member 52, where the distal guide member 52 of FIGS. 14-16 may be employed for the right radius, while the distal guide member 52 of FIGS. 17-19 may be used for the left radius. The distal guide members 52 of FIGS. 14-19 are similar to the proximal guide members of FIGS. 10-13, but provide a different technique for coupling the distal guide member 52 to the proximal guide member 53. More specifically, the hook-shaped portion 84 includes a protrusion 98 that extends across its width, as shown in FIGS. 14 and 17. The protrusion 98 is configured to engage a channel 100 defined in the proximal guide member 53 shown in FIGS. 25-27. Thus, the engagement of the protrusion 98 within the channel 100 may provide additional resistance to rotational movement between the distal 52 and proximal 53 guide members. As before, the distal guide members 52 of FIGS. 14-19 include a fastener 86 that is configured to engage a threaded opening 92 defined in the proximal guide member 53, as well as an alignment pin 88 that is configured to engage an opening 94 defined in the proximal guide member 53.

Figure 24:
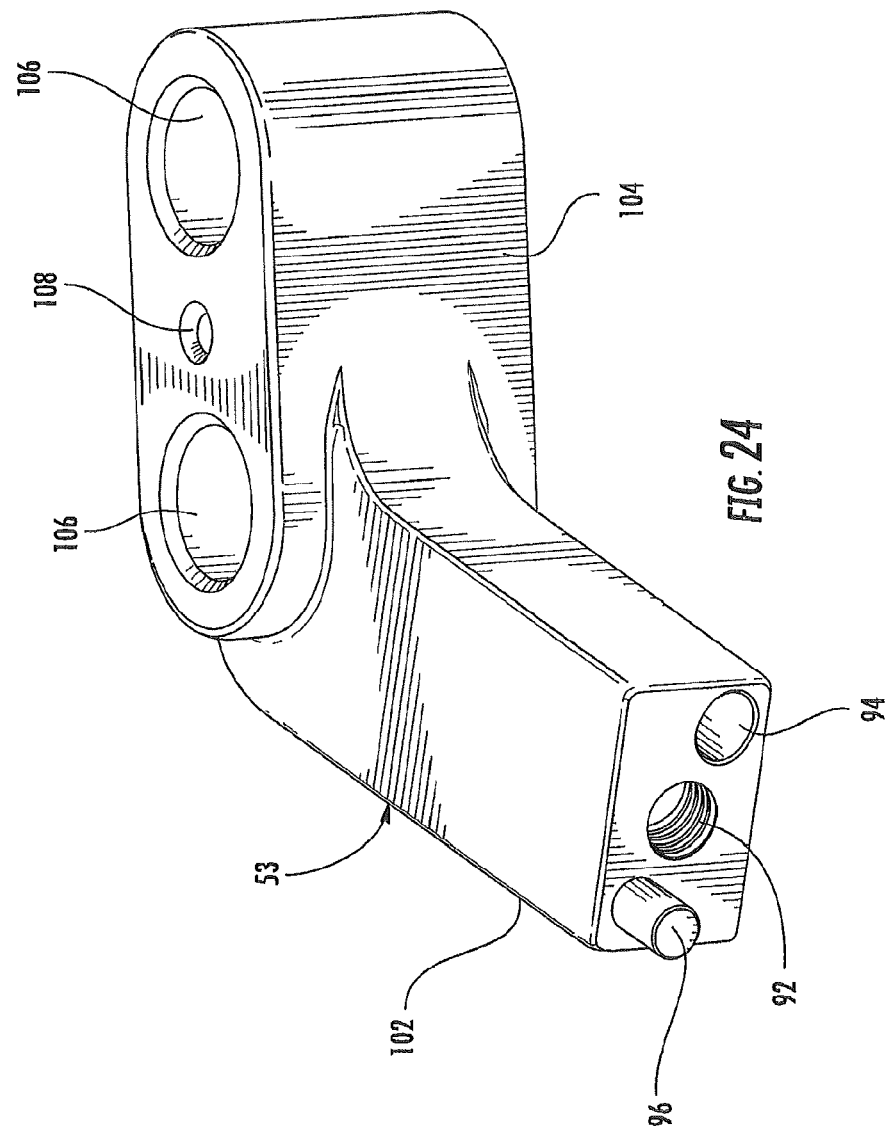
FIG. 24 is a perspective view of the proximal guide member shown in FIG. 23.

The guide assembly 10 further includes a proximal guide member 53 for guiding fasteners 21 within the second end 23 of the fixation member 20 and the second bone fragment 17, as shown in FIGS. 24-28 according to additional embodiments of the present invention. The proximal guide member 53 is configured to engage a respective distal guide member 52, as shown in FIG. 29. In particular, the proximal guide member 53 of FIG. 24 is generally configured to be coupled to the distal guide members 52 shown in FIGS. 10-13.

The proximal guide member 53 is generally L-shaped in configuration and includes a first portion 102 for engaging with the distal guide member 52 and a second portion 104 for guiding respective fasteners 21 into respective openings 36 defined in the fixation member 20. In particular, the second portion 104 includes a plurality of openings 106 that are configured to receive various devices for implanting the fixation member 20, such as a tube protector 72, as shown in FIG. 34. In addition, the second portion 104 includes a smaller opening 108 that could be configured to receive a k-wire 41 or similar device therein.

Figure 26:
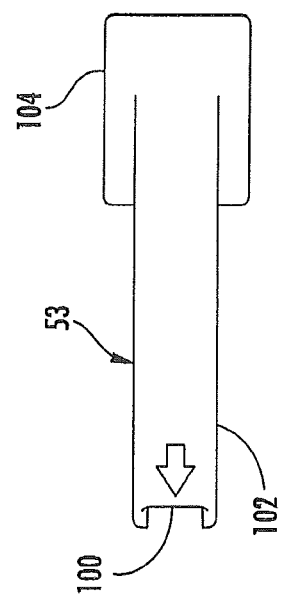
FIGS. 25 and 26 are side elevation views of a proximal guide member according to one embodiment of the present invention.
Figure 25:
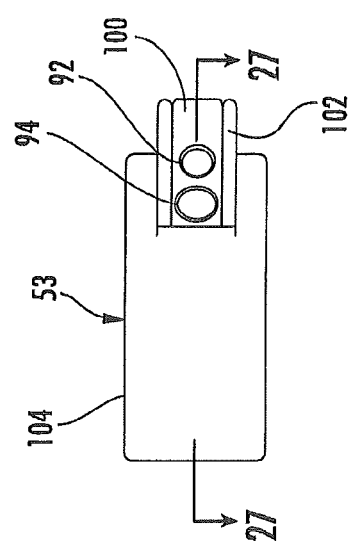
Figure 27:
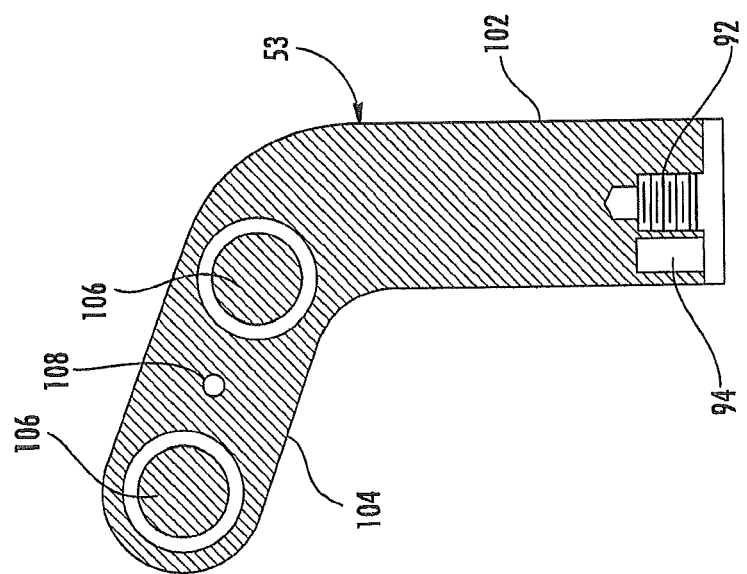
FIG. 27 is a cross-sectional view of the proximal guide member of FIG. 25.
Figure 32:
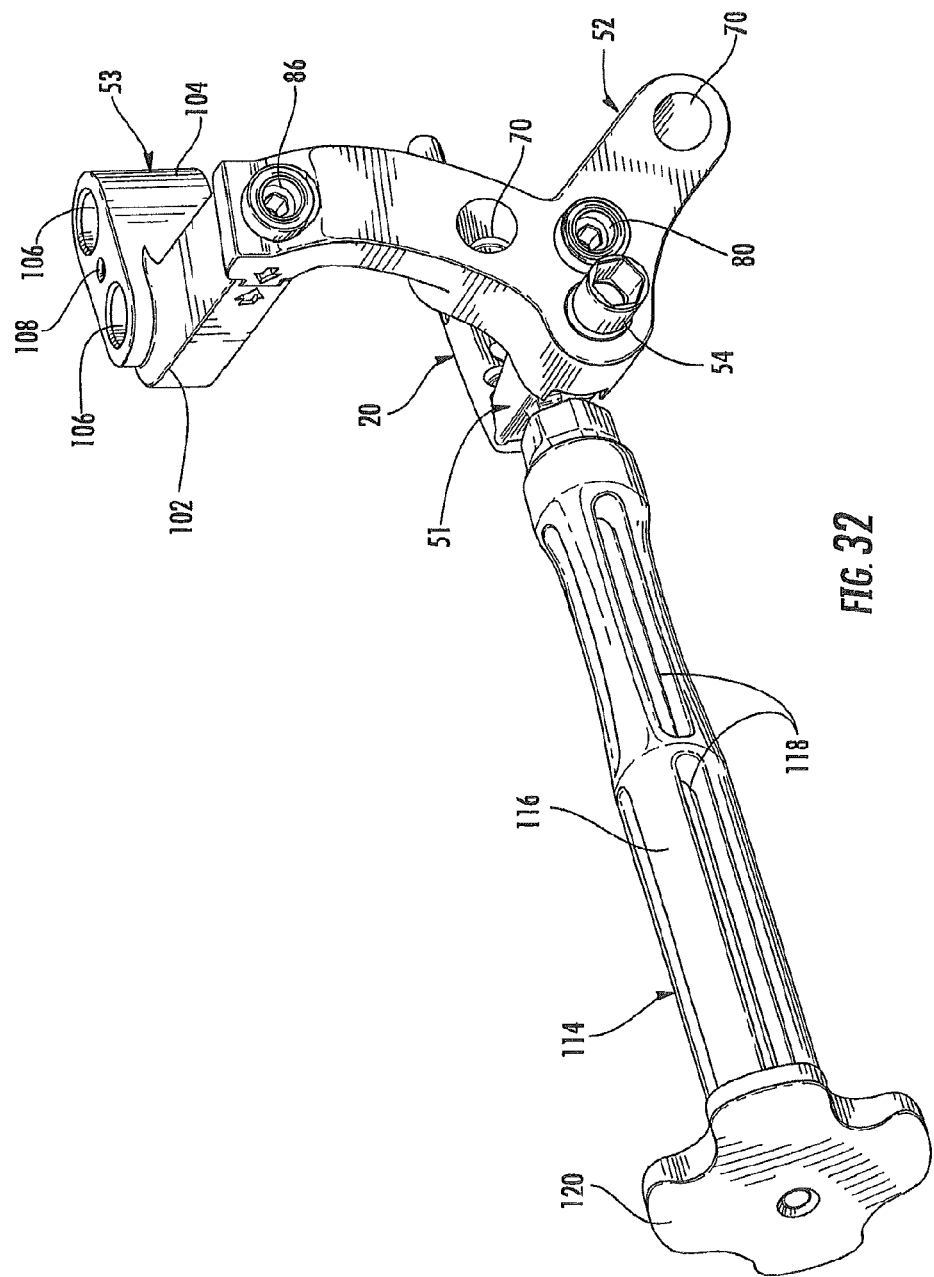
FIGS. 32 and 33 are perspective views of a guide assembly and a handle coupled thereto according to one embodiment of the present invention.
Figure 33:
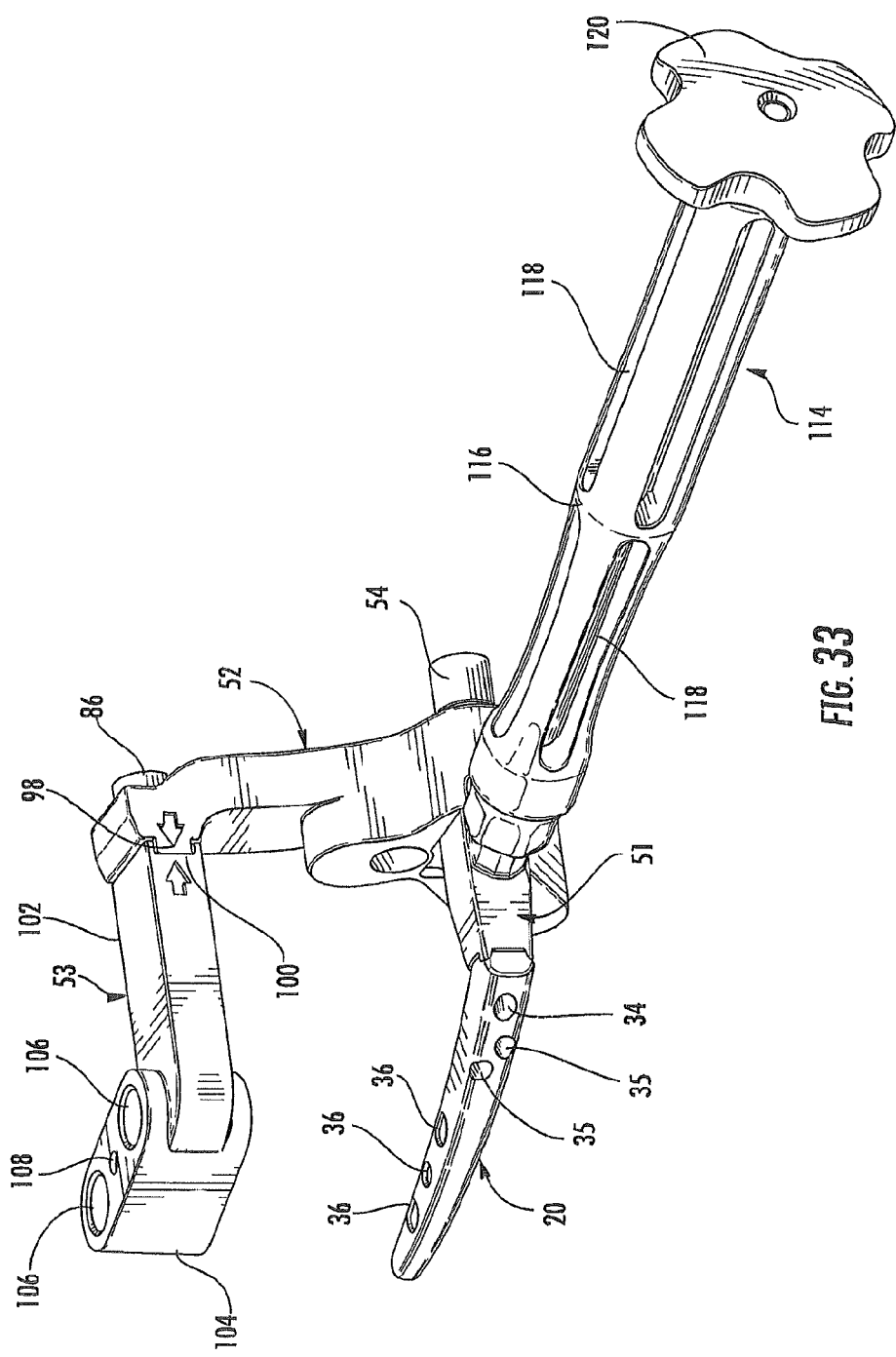

FIGS. 25-27 illustrate a proximal guide member 53 according to an additional embodiment of the present invention, which is configured to be coupled to the distal guide members 52 illustrated in FIGS. 14-19. As described above, the proximal guide member 53 includes a channel 100 that is configured to receive the protrusion 98, as shown in FIGS. 32 and 33. Different proximal guides 53 can also be used for different sized fixation members 20. For example, FIG. 28 shows a proximal guide member 53 having additional openings 106 for accommodating a longer fixation member 20. In addition, the proximal guide member 53 can be employed in right and left handed configurations depending on the type of long bone being treated and the orientation of the side aperture 19.

FIG. 29 illustrates a wrench 110 that is configured to engage various fasteners of the guide assembly 10. For example, FIG. 29 illustrates that the wrench 110 is configured to mate with the head of fastener 86 so as to tighten the threaded end 87 within the threaded opening 92 of the proximal guide member 53. The wrench 110 is also compatible with the head of the guide fastener 54 and fastener 80. Thus, the wrench 110 provides a universal tool that may be used with different fasteners used in assembling the guide assembly 10, as well as securing the guide assembly to the fixation member 20. The wrench 110 may include a plurality of longitudinal slots 112 in order to reduce weight.

As briefly mentioned above, the guide member 51 includes a threaded opening 64 that is configured to receive a handle 114. The handle 114 is typically attached to the guide member 51 in order to facilitate installation of the fixation member 20 through the side aperture 19 and into the medullary canal 15. The handle 114 generally includes a body portion 116 and a plurality of slots 118 defined therein. In addition, the handle 114 may include a strike plate 120 that includes a shaft 121 that extends the length of the body portion 116 and a threaded end 123 that is configured to mate with the threaded opening 64 of the guide member 51, as shown in FIG. 38. Thus, rotation of the strike plate 120 in a counterclockwise or clockwise direction may cause loosening or tightening of the shaft 121 to the guide member 51. Moreover, the surgeon may contact the strike plate 120 with a hammer in order to aid in implanting the fixation member 20 within the radius 11. Because the body portion 116 may receive bone fragments therein as the fixation member 20 is positioned within the radius 11, the slots 118 provide a technique for removing bone fragments or otherwise cleaning any bone fragments removed from the radius while installing the fixation member. FIG. 39 shows that the slots 118 may extend radially within the body portion 116 to the shaft 121. There may be any number of slots 118 defined in the body portion 114, and the slots may extend the entire length of the body portion or include a plurality of axially aligned slots, as shown in FIG. 33.

Figure 35:
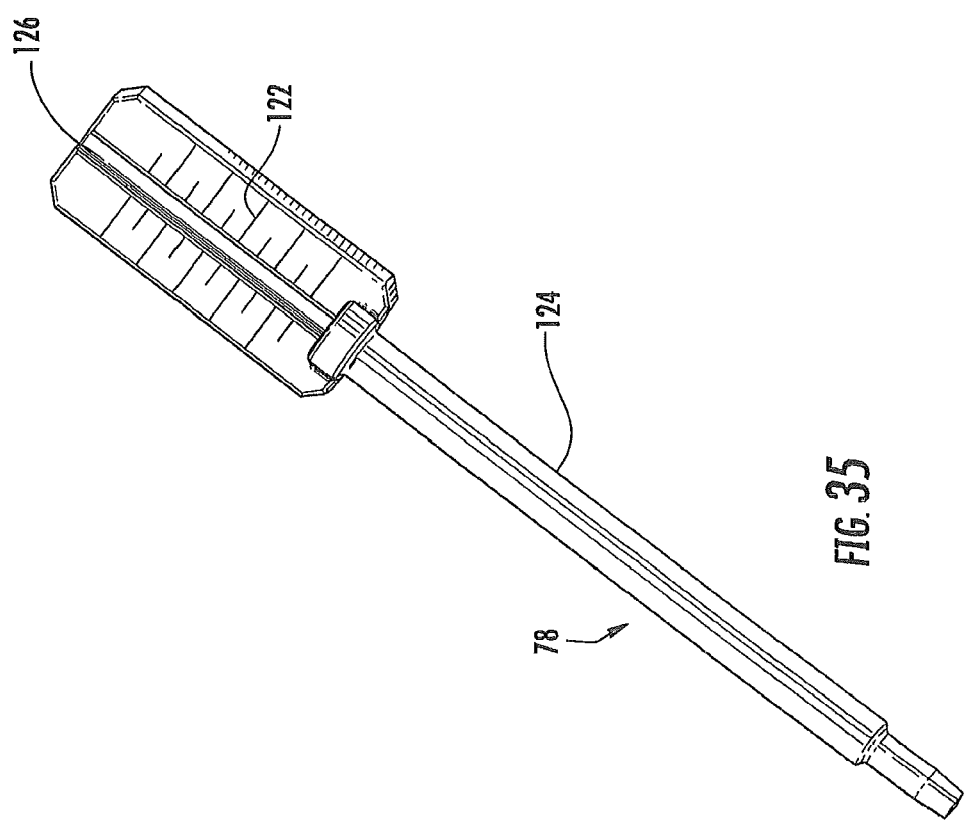
FIG. 35 is a perspective view of a drill guide according to one embodiment of the present invention.
Figure 36:
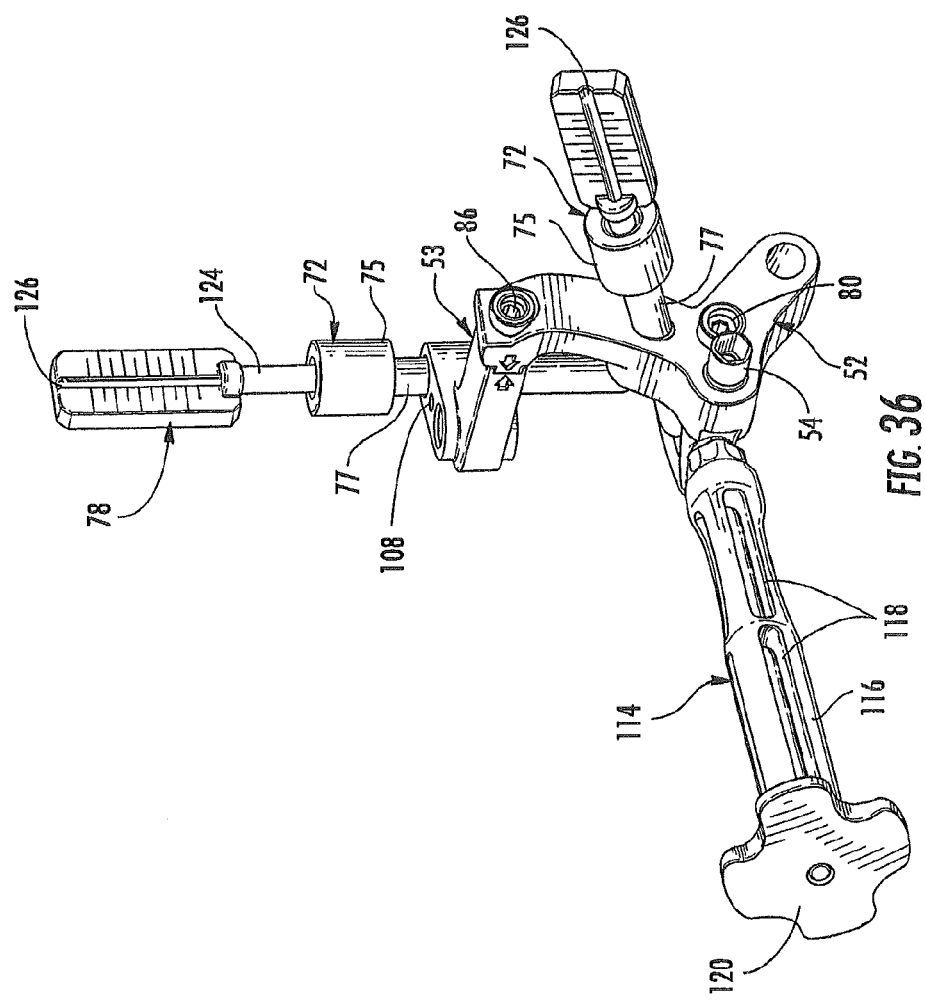
FIG. 36 is a perspective view of a guide assembly including drill guides and respective drill guides positioned therein, according to one embodiment of the present invention.
Figure 37:
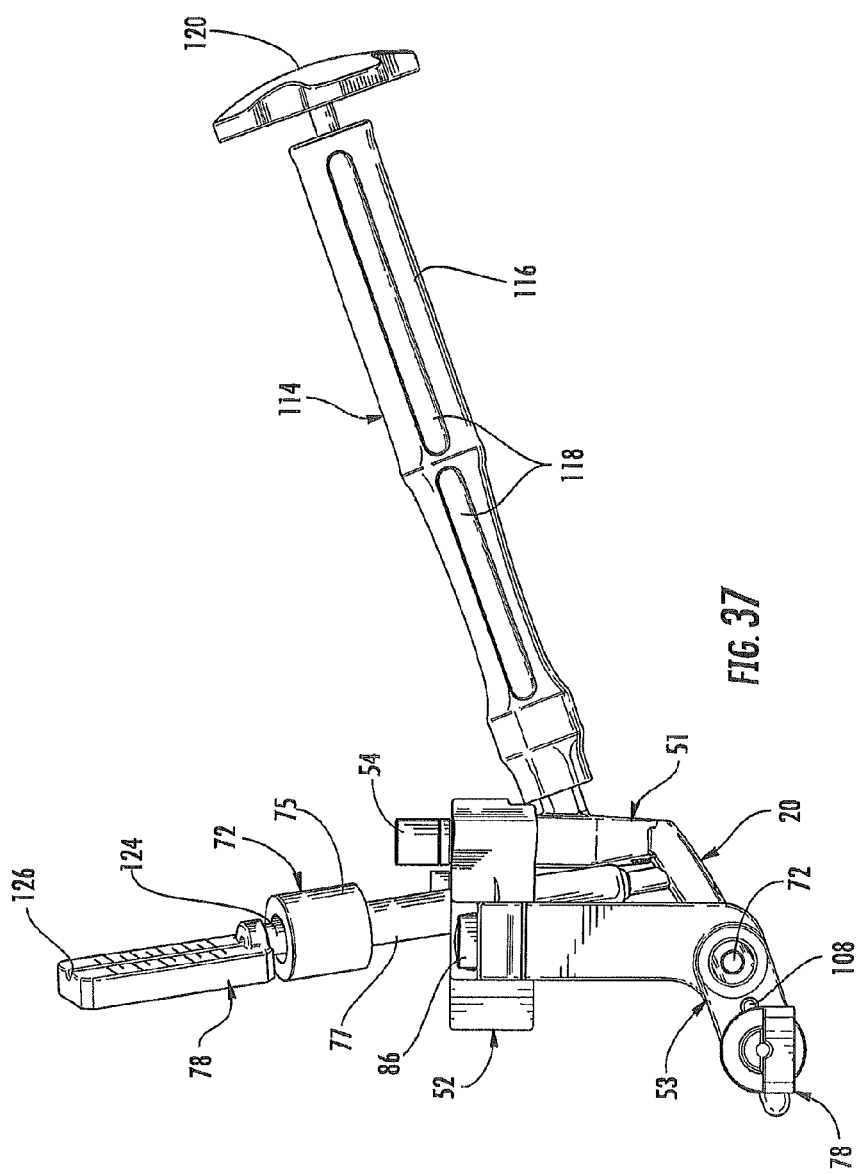
FIG. 37 is a side elevation view of a guide assembly including drill guides and respective drill guides positioned therein, according to one embodiment of the present invention.

The guide assembly 10 also includes a plurality of drill guides 78 as shown in FIG. 1. The drill guides 78 are employed to receive a drill bit, as well as facilitate measurement of the depth of holes drilled within the radius 11. As shown in FIG. 35, the drill guides 78 may include a plurality of measurement indicators 122 that are used by the surgeon to determine a fastener 21 and/or k-wire 41 of the appropriate length based on the depth of the hole within the radius 11. The drill guides 78 include a shaft 124 that is configured to slide within the opening 73 of the tissue protectors 72, through the holes 34, 35, and/or 36, and into the radius 11. In addition, the drill guides 78 include a longitudinal slot 126 that extends the length of the drill guide, which is configured to slidably receive a drill bit or k-wire 41 therein. Defined within the elongate shaft 124 of the drill guide 78 is a guide shaft opening that tapers from a wider to narrower diameter near its distal end. Thus, a dual diameter drill bit could be used to drill a hole within radius 11, wherein the larger diameter of the drill bit prevents travel of the drill bit beyond the shoulder defined near the distal end of the drill guide 78 so as to prevent drilling past a selected depth. As shown in FIG. 1, the depth of the hole drilled in the radius 11 may be determined based on the alignment of a predetermined marking on the k-wire 41 with one of the measurement indicators 122. The k-wire 41 and/or measurement indictors 122 could also employ fluorescent paint or grooved notches to facilitate reading of the measurements. In addition, the drill guides 78 are capable of being removed from respective tissue protectors 72 while k-wires 41 are inserted therein, which may aid the surgeon in viewing the k-wire within the radius 11. The tissue protectors 72 could also be removed from the distal 52 and proximal 53 guide members while the k-wires 41 are inserted within the radius 11 in order to visualize the radius 11 if desired.

The distal 52 and proximal 53 members may be a radiolucent material. Thus, the distal 52 and proximal 53 guide members do not obstruct images taken of the radius during implantation of the fixation member 20, such as images taken using radiographic techniques. For example, the radiolucent material could be a carbon reinforced PEEK material, which is lighter than conventional stainless steel guide assemblies. A guide assembly 10 comprising a lighter material may be easier to handle by a surgeon and apply less torque on the bone fragments. Moreover, other components of the guide assembly could be a radiolucent material, such as the tissue protectors 72, k-wires 41, and/or handle body 116, in order to reduce weight of the guide assembly 10, as well as provide better visualization of the fixation member 20 within the radius during surgery.

In order to install the fixation member 20, a side aperture 19 is cleared in a lateral side of the radius 11, and a conventional bone awl (not shown) may be used to open the medullary canal 15 of cancellous bone. A trialing broach may be urged through the side aperture 19 and into the medullary canal 15 to approximate the size of the fixation member 20. Other conventional tools could also be employed to clear bone, such as reamers and awls.

Once the side aperture 19 has been formed and the medullary canal 15 cleared and sized, an appropriately sized fixation member 20 may be selected. The handle 114 is attached to the threaded opening 64 defined in the guide member 51, as shown in FIGS. 32-34. The guide member 51 may then be attached to the fixation member 20 via the guide fastener 54. In particular, the threaded tip 58 of the guide fastener 54 may be advanced into the threaded opening 34 of the fixation member 20, which mates the prongs 60 with the indentations 40, thereby locking out micro-motion and rotation between the guide member 51 and the fixation member 20. The handle 114 may then be used to orient the fixation member 20 through the side aperture 19 and into the medullary canal 15. The handle 114 may then be then unscrewed from the guide member 51.

The distal guide member 52 may then be attached to the guide member 51 by inserting the protrusion 66 within the slot 76 and tightening the fastener 80 to the threaded opening 68, as shown in FIGS. 20 and 21. The proximal guide member 53 may then be attached to the distal guide member 52 by sliding the protrusion 98 within the channel 100 such that the alignment pin 88 aligns with the opening 94. The fastener 86 may then be tightened to secure the threaded end 87 within the threaded opening 92.

The surgeon may then insert tissue protectors 72 within each of the openings 70 of the distal guide member 52 and the openings 106 of the proximal guide member 53. For temporary fixation, a k-wire 41 may be inserted within the smaller guide openings 36, 108 of the distal 52 and proximal 53 guide members, respectively. The drill guides 78 may then be placed into respective tissue protectors 72, as well as within the guide fastener 54. A drill bit (not shown) may be advanced into the drill guides 78 to form pilot holes in the radius 11.

The depth of these holes may then be tested using measurement indicators 122 by inserting a k-wire within the longitudinal slot 126 of the drill guides 78, as shown in FIG. 1. The depth measurements facilitate selection of fasteners 21 of the appropriate length. If necessary, the drilled holes are then tapped to prepare them for insertion of threaded fasteners 21. After tapping, the threaded fasteners 21 may be advanced through the aligned openings 34, 35, 36, 106 in the fixation member 20 and the radius 11 so as to connect the bone fragments 16, 17, as shown in FIG. 2. The guide assembly 10 can then be removed by unscrewing the guide fastener 54.

It is understood that various techniques could be used to install the fixation member 20 within the radius 11, as the particular order of steps discussed above need not be limiting, as the particular procedure may depend on various factors, such as the surgeon or the patient. For example, the distal guide member 52 could be attached to the guide member 51 prior to inserting the fixation member 20 within the medullary canal 15. For additional and alternative details regarding a guide assembly and methods for installing a fixation member within a long bone according to various embodiments of the present invention, Applicants hereby incorporate by reference U.S. Patent Appl. Publ. No. 2006/0015123, filed Jul. 15, 2004, herein in its entirety.

The present invention may provide several advantages. For example, the guide member 51 may be coupled to the fixation member 20 without first having to attach the distal guide member 52 and/or proximal guide member 53. Thus, the surgeon may be able to more easily position the fixation member 20 within the radius 11 since the surgeon will have a better view of the radius and will have a lighter device to manipulate. In addition, the distal guide member 52 is interchangeable with the guide member 51 such that the surgeon could remove the distal guide member 52 during surgery, such as for better visualization or to change to a different size. Thus, attachment of the guide member 51 to the fixation member 20 with the guide fastener 54 provides a secure engagement that allows the distal guide member 52 to be attached and removed when desired. Similarly, the proximal guide member 53 is interchangeable with the distal guide member 52 such that the proximal guide member may be selectively engaged to and disengaged from the proximal guide member. Therefore, the combination of the guide member 51, distal guide member 52, and proximal guide member 53 provides interchangeable components for a more universal guide assembly 10.

Furthermore, the distal 52 and proximal 53 members may be a radiolucent material, which also enhances visualization during surgery, as well as reduces the weight of the guide assembly, thereby resulting in easier manipulation of the assembly and less torque on the bone fragments. The distal 52 and proximal 53 guide members are also configured to be spaced away from the patient's radius 11 such that the guide assembly 10 is adaptable to various sized patients. In addition, the offset distance between the distal 52 and proximal 53 guide members from the patient's skin allows tissue protectors 72 to be placed within each of the holes 70, 106 in order to provide additional protection from injuring the patient's skin during installation of the fixation member 20.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for placing a fixation member within a medullary canal of a radius, the method comprising:
    defining a side aperture in the radius that extends into a medullary canal thereof;
    attaching a guide member to the fixation member with a guide fastener;
    inserting the fixation member through the side aperture until the fixation member is positioned in the medullary canal;
    attaching an interchangeable distal guide member to the guide member after the fixation member is positioned in the medullary canal, wherein the distal guide member defines a plurality of fastener guide openings;
    defining a plurality of fastener openings within the radius via the plurality of fastener guide openings defined in the distal guide member that align with a plurality of fastener openings defined in the fixation member; and
    advancing a plurality of bone fasteners through the plurality of fastener guide openings defined in the distal guide member and the plurality of fastener openings defined in the fixation member and the radius.

2. A method of claim 1, further comprising attaching an interchangeable proximal guide member to the distal guide member, wherein the proximal guide member defines a plurality of fastener guide openings.

3. A method of claim 2, further comprising defining a plurality of fastener openings within the radius via the plurality of fastener guide openings defined in the proximal guide member that align with a plurality of fastener openings defined in the fixation member that are located proximally of the plurality of fastener openings defined via the distal guide member.

4. A method of claim 1, further comprising detaching the distal guide member from the guide member while the member is attached to the fixation member.

5. A method of claim 1, wherein inserting the fixation member through the side aperture comprises inserting the fixation member through a lateral surface of a widened end of the radius subjacent an articular cartilage surface.

6. A method of claims 1, wherein inserting the fixation member through the side aperture comprises inserting the fixation member through the radial styloid process.

7. A method of claim 1, wherein defining the fastener openings within the radius via the distal guide member comprises defining at least three of the fastener openings within the radius, and
    wherein advancing the bone fasteners through the fastener guide openings defined in the distal guide member and the fastener openings defined in the fixation member and the radius comprises advancing at least three of the bone fasteners.

8. A method of claim 1, wherein one of the fastener openings defined in the fixation member defines a guide portion and a fastener portion,
    wherein attaching the guide member to the fixation member with the guide fastener comprises engaging the guide fastener with the guide portion, and
    wherein advancing the bone fasteners through the fastener openings defined in the fixation member comprises engaging one of the bone fasteners with the fastener portion.

9. A method of claim 1, further comprising detaching the distal guide member from the guide member while the guide member is attached to the fixation member by the guide fastener.

10. A method of claim 1, wherein inserting the fixation member through the side aperture comprises positioning the fixation member such that the fixation member extends out of the side aperture.

11. A method of claim 1, wherein attaching the distal guide member to the guide member comprises aligning a first fastener guide opening defined in the guide member with a second fastener guide opening defined in the distal guide member, and
    wherein attaching the guide member to the fixation member with the guide fastener comprises inserting the guide fastener through the first fastener guide opening and the second fastener guide opening.

12. A method of claim 11, wherein attaching the distal guide member to the guide member further comprises inserting a protrusion defined by the guide member, through which the first fastener guide opening extends, into the second fastener guide opening.

13. A method of claim 1, wherein defining the fastener openings within the radius comprises inserting a drill guide through an opening extending through the guide fastener.

14. A method of claim 1, wherein attaching the distal guide member to the guide member comprises inserting at least a portion of the guide member into a clot defined in the distal guide member.

15. A method of claim 1, further comprising respectively inserting a tissue protector through each of the fastener guide openings of the proximal guide member and the fastener guide openings of the distal guide member.

16. A method of claim 15, further comprising respectively inserting a drill guide through each tissue protector.

17. A method of claim 16, further comprising respectively inserting a k-wire through each drill guide in order to determine a depth of drilling into the radius based on a measurement reading on each drill guide.

18. A method of claim 4, wherein attaching the proximal guide member to the distal guide member comprises attaching the proximal guide member to the distal guide member via threaded engagement.

19. A method of claim 4, wherein attaching the proximal guide member to the distal guide member comprises engaging an alignment pin of the distal guide member with an opening defined in the proximal guide member.

\* \* \* \* \*

UNITED STATES PATENT AND TRADEMARK OFFICE
CERTIFICATE OF CORRECTION

| | | |
|---|---|---|
| PATENT NO. | : 9,662,153 B2 | Page 1 of 1 |
| APPLICATION NO. | : 14/271067 | |
| DATED | : May 30, 2017 | |
| INVENTOR(S) | : Scott Larsen, Virak Tan and Mark J. Warburton | |

It is certified that error appears in the above-identified patent and that said Letters Patent is hereby corrected as shown below:

At Column 12, Line 2, Change "trialing" to --trialling--.

Signed and Sealed this
Twentieth Day of February, 2018

Andrei Iancu
*Director of the United States Patent and Trademark Office*